US012571758B2

(12) United States Patent
Masakari

(10) Patent No.: US 12,571,758 B2
(45) Date of Patent: Mar. 10, 2026

(54) GLUCOSE REDOX REACTION AND COMPOSITION FOR GLUCOSE MEASUREMENT USING FLAVIN COMPOUND

(71) Applicant: KIKKOMAN CORPORATION, Noda (JP)

(72) Inventor: Yosuke Masakari, Noda (JP)

(73) Assignee: KIKKOMAN CORPORATION, Noda (JP)

( * ) Notice: Subject to any disclaimer, the term of this patent is extended or adjusted under 35 U.S.C. 154(b) by 0 days.

(21) Appl. No.: 16/342,841

(22) PCT Filed: Oct. 19, 2017

(86) PCT No.: PCT/JP2017/037851
§ 371 (c)(1),
(2) Date: Apr. 17, 2019

(87) PCT Pub. No.: WO2018/074551
PCT Pub. Date: Apr. 26, 2018

(65) Prior Publication Data

US 2019/0257781 A1 Aug. 22, 2019

(30) Foreign Application Priority Data

Oct. 19, 2016 (JP) ................................ 2016-205539

(51) Int. Cl.
*G01N 27/327* (2006.01)
*C12M 1/34* (2006.01)
(Continued)

(52) U.S. Cl.
CPC ........... *G01N 27/3271* (2013.01); *C12M 1/34* (2013.01); *C12Q 1/004* (2013.01); *C12Q 1/26* (2013.01);
(Continued)

(58) Field of Classification Search
CPC .... G01N 27/3271; G01N 27/327; C12Q 1/32; C12Q 1/26; C12Q 1/54; C12Q 1/004; C12Q 1/006; C12M 1/34
See application file for complete search history.

(56) References Cited

U.S. PATENT DOCUMENTS 4,704,193 A * 11/1987 Bowers .................. C12Q 1/003
204/403.14
5,089,112 A * 2/1992 Skotheim ............... C12Q 1/004
600/347
(Continued)

FOREIGN PATENT DOCUMENTS

EP 0390390 A1 10/1990
EP 0800086 A1 10/1997
(Continued)

OTHER PUBLICATIONS

Katz et al. (E Katz, A Riklin, V Heleg-Shabtai, I Willner, A Buckmann, Glucose oxidase electrodes via reconstitution of the apo-enzyme: tailoring of novel glucose biosensors, Analytica Chimica Acta 385 (1999) 45-58). (Year: 1999).*
(Continued)

*Primary Examiner* — Shizhi Qian
(74) *Attorney, Agent, or Firm* — Lucas & Mercanti, LLP

(57) ABSTRACT

This invention provides an improved method for electrochemical glucose measurement and an improved composition for glucose measurement. This invention also provides a composition for glucose measurement comprising a flavin compound. This invention also provides an electrode comprising a flavin compound and a sensor and a glucose fuel cell comprising such electrode. In addition, this invention provides a method for electrochemical glucose measurement and a method for electric power generation using a flavin compound. The flavin compound of the present invention is
(Continued)

non-toxic or less toxic and it can be thus used for a means of self-contained continuous glucose measurement.

8 Claims, 9 Drawing Sheets

Specification includes a Sequence Listing.

(51) Int. Cl.

| | |
|---|---|
| ***C12Q 1/00*** | (2006.01) |
| ***C12Q 1/26*** | (2006.01) |
| ***C12Q 1/32*** | (2006.01) |
| ***C12Q 1/54*** | (2006.01) |
| ***H01M 4/90*** | (2006.01) |
| ***H01M 8/16*** | (2006.01) |

(52) U.S. Cl.

CPC ................. *C12Q 1/32* (2013.01); *C12Q 1/54* (2013.01); *G01N 27/327* (2013.01); *H01M 4/90* (2013.01); *H01M 8/16* (2013.01); *Y02E 60/50* (2013.01)

(56) References Cited

U.S. PATENT DOCUMENTS

| | | | | |
|---|---|---|---|---|
| 5,126,247 | A | 6/1992 | Palmer et al. | |
| 5,445,920 | A | 8/1995 | Saito | |
| 5,710,009 | A * | 1/1998 | Fitzpatrick | G01N 33/94 435/7.9 |
| 6,350,368 | B1 * | 2/2002 | Willner | C12Q 1/004 205/777.5 |
| 2004/0101741 | A1 * | 5/2004 | Minteer | H01M 8/16 429/506 |
| 2005/0196820 | A1 * | 9/2005 | Zweig | G01N 33/5438 435/14 |
| 2005/0249633 | A1 * | 11/2005 | Blatt | G01N 35/00009 422/400 |
| 2006/0292661 | A1 * | 12/2006 | Gilbert | B82Y 30/00 549/3 |
| 2007/0289880 | A1 * | 12/2007 | Zweig | C12Q 1/34 205/777.5 |
| 2008/0248354 | A1 * | 10/2008 | Kubo | H01M 8/16 429/458 |
| 2009/0101498 | A1 * | 4/2009 | Papadimitrakopoulos | C01B 13/0259 204/403.11 |
| 2010/0261072 | A1 * | 10/2010 | Tsugawa | G01N 27/3273 429/401 |
| 2013/0161204 | A1 | 6/2013 | Uchiyama et al. | |
| 2018/0340211 | A1 | 11/2018 | Masakari et al. | |
| 2018/0355022 | A1 | 12/2018 | Masakari et al. | |
| 2019/0136285 | A1 | 5/2019 | Masakari et al. | |
| 2019/0185907 | A1 | 6/2019 | Masakari | |

FOREIGN PATENT DOCUMENTS

| | | | |
|---|---|---|---|
| JP | H01-317425 | A | 12/1989 |
| JP | H02298855 | A | 12/1990 |
| JP | H0321857 | A | 1/1991 |
| JP | H06-242068 | A | 9/1994 |
| JP | H1010130 | A | 1/1998 |
| JP | 2004-296099 | A | 10/2004 |
| JP | 2006-234788 | A | 9/2006 |
| JP | 2007-509355 | A | 4/2007 |
| JP | 2008-71584 | A | 3/2008 |
| JP | 2009-150658 | A | 7/2009 |
| JP | 2009-168622 | A | 7/2009 |
| JP | 2014018096 | A | 2/2014 |
| WO | 2005/040407 | A1 | 5/2005 |
| WO | 2008/032871 | A2 | 3/2008 |
| WO | 2012/042903 | A1 | 4/2012 |

OTHER PUBLICATIONS

Willner et al. (I Willner, V Heleg-Shabtai, R Blonder, E Katz, G Tao, Electrical wiring of glucose oxidase by reconstitution of FAD-modified monolayers assembled onto Au-electrodes, J. Am. Chem. Soc. 118 (1996) 10321-10322) (Year: 1996).*

Dervisevic et al. (M Dervisevic, E Cevik, M Senel, Development of glucose biosensor based on reconstitution of glucose oxidase onto polymeric redox mediator coated pencil graphite electrodes, Enzyme and Microbial Technology 68 (2014) 69-76) (Year: 2014).*

Godet et al. (C Godet, M Boujtita, NE Murr, Direct electron transfer involving a large protein: glucose oxidase, New. J. Chem. 23 (1999) 795-797) (Year: 1999).*

Wingard et al. (LB Wingard, K Narasimhan, Immobilized Flavin Coenzyme Electrodes for Analytical Applications, Methods in Enzymology 137 (1988) 103-111). (Year: 1988).*

Durliat et al. (H Durliat, MB Barrau, M Comtat, FAD used as a mediator in the electron transfer between platinum and several biomolecules, Bioelectrochemistry and Bioenergetics 19 (1988) 413-423) (Year: 1988).*

Zhang et al.,A comparative study on STM imaging and electrocatalytic activity of different surfaces modified with flavin adenine dinucleotide, Electrochimica Acta, 1995, 40(6), 733-744 (Year: 1995).*

TDK Corporation, Partial English translation of relevant passages, specifically paragraph [0029] and example 7, for JP 2009-150658A, published Jul. 9, 2019 (2 pages).

TDK Corporation, Partial English translation of relevant passages, specifically paragraph [0037] and example 1, for JP 2009-168622A, published Jul. 30, 2009 (2 pages).

Fujifilm Corporation, Partial English translation of relevant passages, specifically examples 1-3, for JP 2004-296099A, published Oct. 21, 2004 (2 pages).

Durliat et al., "FAD used as a mediator in the electron transfer between platinum and several biomolecules", Bioelectrochemistry and Bioenergetics, vol. 19, Issue 4, pp. 413-423.

Office Action for Corresponding Japanese Application No. 2017-203338, Sep. 28, 2021, 2 Pages.

* cited by examiner

GLUCOSE REDOX REACTION AND COMPOSITION FOR GLUCOSE MEASUREMENT USING FLAVIN COMPOUND

CROSS-REFERENCE TO RELATED APPLICATIONS

This application is a 371 of PCT/JP2017/037851, filed Oct. 19, 2017, which claims benefit of Japanese Patent Application No. 2016-205539 filed on Oct. 19, 2016.

TECHNICAL FIELD

The present invention relates to glucose redox reaction using a flavin compound and a composition containing a flavin compound. More specifically, the present invention relates to a method for glucose measurement involving the use of a flavin compound as a mediator for glucose oxidase or glucose dehydrogenase. The present invention also relates to a composition for glucose measurement containing a flavin compound that may be effectively used as a diagnostic reagent for diabetes, as a glucose sensor, or for a kit for glucose measurement.

BACKGROUND ART

Glucose measurement is used for blood glucose monitoring of diabetic patients and the like. Glucose quantification generally involves the use of glucose oxidase (hereinafter, also referred to as GOD) and glucose dehydrogenase (hereinafter, also referred to as GDH). Such enzymes are used in self-measurement apparatuses for blood glucose level that can be used at home (SMBG) or continuous glucose measurement apparatuses (also referred to as CGM or FGM).

Glucose oxidase is an oxidoreductase, which catalyzes the reaction of oxidizing β-D-glucose into D-glucono-1,5-lactone (gluconolactone). Glucose oxidase uses oxygen as the electron acceptor and flavin adenine dinucleotide (FAD) as a cofactor.

Glucose dehydrogenase is classified as an oxidoreductase, uses glucose and an electron acceptor as substrates, and catalyzes a reaction which generates gluconolactone and a reduced-form acceptor. Examples of glucose dehydrogenase include nicotinamide dinucleotide-dependent GDH, nicotinamide dinucleotide phosphate-dependent GDH, pyrroloquinoline quinone (PQQ)-dependent GDH, and FAD-dependent GDH (flavin-binding type GDH).

When GOD is used for glucose measurement, a hydrogen peroxide electrode may be used. In this method, a voltage of +0.6 V (vs. Ag/AgCl) to +0.9 V (vs. Ag/AgCl) is applied to the hydrogen peroxide electrode, and the hydrogen peroxide generated when gluconolactone is produced from glucose is measured. This method is mainly used in SMBG and CGM. However, this method is disadvantageously influenced by contaminants such as ascorbic acid contained in the measurement solution because of the application of a relatively high voltage.

In order to overcome such drawback, a method involving the use of an artificial electron mediator (hereinafter, also referred to simply as a mediator) instead of hydrogen peroxide was developed. In this method, upon enzymatic conversion of glucose into gluconolactone, an oxidized-form mediator is converted into a reduced-form mediator. The reduced-form mediator transfers an electron to the electrode and returns to the oxidized-form mediator. An advantage of the method using a mediator is that the applied voltage can be lowered compared to the method using a hydrogen peroxide electrode. However, conventional mediators were problematic in terms of high cost and toxicity. For example, a metal complex such as potassium ferricyanide, which is a typical mediator, may be deleterious if it enters the human body.

As other conventional mediators, quinones, phenazines, viologens, cytochromes, phenoxazines, phenothiazines, ferricyanides such as potassium ferricyanide, ferredoxins, ferrocenes or ferrocene derivatives, osmium complexes, and the like were known.

In the cases of GOD and GDH, the cofactor FAD is often embedded within the enzyme molecule and, therefore, when GOD and GDH are used for glucose measurement, accordingly, it is generally not possible to transfer the electron to the electrode in the absence of a mediator. However, mediators are expensive and difficult to immobilize onto an electrode surface. When measuring glucose of a diabetic patient, for example, using a mediator for a CGM or FGM apparatus without immobilization thereof onto an electrode may cause the mediator present in the measurement solution to flow into the body. However, because mediators are bio-incompatible or toxic in many cases, it is undesirable for the mediator to flow into the body. Accordingly, methods of glucose measurement using conventional mediators are not suitable for CGM or FGM apparatuses and extra measures to avoid the mediator from flowing into the body are required.

Patent Literature 1 discloses a mediator compound capable of suppressing changes in current values between before and after the reagent storage period.

Patent Literature 2 discloses a biosensor involving the use of an oxidoreductase. As a mediator compound, for example, ferrocyanide compounds are used.

Patent Literature 3 discloses a redox reaction involving the use of an electron transfer agent.

While fuel cells have drawn increasing attention, conventional fuel cells often involve the use of platinum and, an artificial compound such as an osmium complex is used as the electron transfer mediator. Platinum is expensive, and artificial compounds involve waste disposal costs because of their toxicity. Under such circumstances, a fuel cell using an enzyme electrode instead of platinum has been reported (e.g., Patent Literature 4). The mediator used in Patent Literature 4 is a metal complex.

With regard to FAD-dependent GDHs (flavin-binding type GDHs), when a polypeptide is synthesized from mRNA encoding the same the polypeptide folds, it is known that FAD is taken into the FAD binding site. As such, an active FAD-dependent GDH is non-covalently bound to FAD (holoenzyme). Further, it is known that FAD-dependent GDH not bound to FAD does not exist stably (apoenzyme). In contrast, NAD-dependent GDH can exist in the form of an apoenzyme, and, therefore, external addition of NAD is necessary to exert activity. In general, it is known that FAD-dependent GOD takes up FAD into the FAD binding site at the time of protein expression, although certain types of FAD-dependent GODs can exist in apoform.

BACKGROUND ART LITERATURE

Patent Literature

[Patent Literature 1] WO 2012/042903

[Patent Literature 2] JP 2007-509355 A (JP Patent No. 4,839,219)

[Patent Literature 3] JP H1-317425 A (1989) (JP Patent No. 3,071,790)

[Patent Literature 4] JP 2008-71584 A

SUMMARY OF INVENTION

Technical Problem

It is an object of the present invention to provide a method for electrochemical glucose measurement and a composition for glucose measurement that can overcome the problems mentioned above. It is another object of the present invention to provide an improved glucose fuel cell and a method for electric power generation.

Solution to Problem

The present inventor has carried out concentrated studies in order to attain the above objects. As a result, the present inventor discovered that a flavin compound can serve as a mediator in a glucose redox reaction catalyzed by an enzyme. This has led to the completion of the present invention.

Without wishing to be bound by any specific theory, each compound has its own oxidoreduction potential. In general, a free-type flavin compound has a more negative oxidoreduction potential (i.e., a lower oxidoreduction potential), compared with an oxidoreduction potential of a flavin compound in the flavoprotein. For example, the oxidoreduction potential of free-type FAD (−0.219 V (vs. NHE)) is lower than the oxidoreduction potential of FAD in flavoprotein (about 0 V (vs. NHE)) (Biochemistry by Voet, Volume 1, 2nd edition, Chapter 15). In this case, in theory, it is believed that an electron will not be transferred from a compound with a higher oxidoreduction potential to a compound with a lower oxidoreduction potential. In the present invention, however, a mixed system of a flavoprotein and a free-type flavin compound was subjected to electrochemical measurement and an electric current was observed. In view of the above, this is a surprising finding.

The present invention encompasses the following.

[1] A composition for glucose measurement comprising a free-type flavin compound and a purified FAD-dependent glucose oxidase or purified FAD-dependent glucose dehydrogenase, wherein the composition:
- (i) does not comprise an externally added artificial electron mediator capable of accepting an electron on its own from an FAD-dependent glucose oxidase or FAD-dependent glucose dehydrogenase;
- (ii) does not comprise an externally added water-insoluble electron mediator capable of accepting an electron on its own from an FAD-dependent glucose oxidase or FAD-dependent glucose dehydrogenase; or
- (iii) does not comprise an externally added electron mediator capable of accepting an electron on its own from an FAD-dependent glucose oxidase or FAD-dependent glucose dehydrogenase and having an oxidoreduction potential of 0.3 V or higher.

[2] An anode electrode comprising a free-type flavin compound and a purified FAD-dependent glucose oxidase or purified FAD-dependent glucose dehydrogenase, wherein the electrode:
- (i) does not comprise an externally added artificial electron mediator capable of accepting an electron on its own from an FAD-dependent glucose oxidase or FAD-dependent glucose dehydrogenase;
- (ii) does not comprise an externally added water-insoluble electron mediator capable of accepting an electron on its own from an FAD-dependent glucose oxidase or FAD-dependent glucose dehydrogenase; or
- (iii) does not comprise an externally added electron mediator capable of accepting an electron on its own from an FAD-dependent glucose oxidase or FAD-dependent glucose dehydrogenase and having an oxidoreduction potential of 0.3 V or higher.

[3] A glucose fuel cell comprising the anode electrode according to [2], a cathode electrode, and a fuel tank containing glucose.

[4] A glucose sensor comprising a free-type flavin compound and a purified FAD-dependent glucose oxidase or purified FAD-dependent glucose dehydrogenase, wherein the sensor:
- (i) does not comprise an externally added artificial electron mediator;
- (ii) does not comprise an externally added water-insoluble electron mediator; or
- (iii) does not comprise an externally added electron mediator having an oxidoreduction potential of 0.3 V or higher.

[5] The electrode according to [2], the fuel cell according to [3], or the sensor according to [4], wherein the flavin compound is a non-enzymatic flavin compound immobilized on a solid phase.

[6] The electrode according to [2] or [5], the fuel cell according to [3] or [5], or the sensor according to [4] or [5], wherein the purified FAD-dependent glucose oxidase or purified FAD-dependent glucose dehydrogenase is immobilized on a solid phase.

[7] The composition according to [1], the electrode according to [2], [5], or [6], the fuel cell according to [3], [5], or [6], or the sensor according to [4], [5], or [6], wherein the flavin compound is a compound represented by Formula (I):

(I)

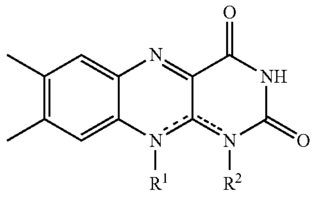

wherein $R^1$ is not present or represents —$CH_3$ or:

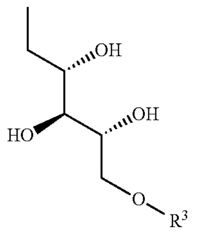

and, when $R^1$ is not present (absent), the nitrogen atom depicted as being bound to $R^1$ forms a double bond with the adjacent carbon atom and $R^2$ represents H, $R^2$ is not present or represents H, and, when $R^2$ is not present, the nitrogen atom depicted as being bound to $R^2$ forms a double bond with the adjacent carbon atom, and $R^3$ represents H, a phosphoric acid group, or:

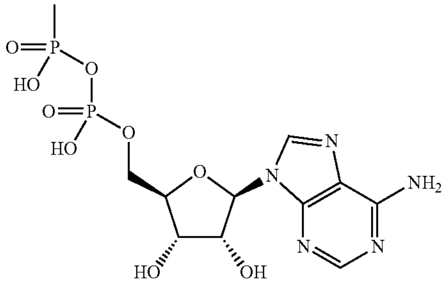 [SMILES: CP(=O)(O)OP(=O)(O)OC[C@H]1O[C@@H](n2cnc3c(N)ncnc32)[C@H](O)[C@@H]1O]

[8] The composition according to [1] or [7], the electrode according to [2], [5], [6], or [7], the fuel cell according to [3], [5], [6], or [7], or the sensor according to [4], [5], [6], or [7], wherein the flavin compound is flavin mononucleotide, riboflavin, lumichrome, flavin adenine dinucleotide, or lumiflavin.

[9] The composition according to [1], [7], or [8], the electrode according to [2], [5], [6], [7], or [8], the fuel cell according to [3], [5], [6], [7], or [8], or the sensor according to [4], [5], [6], [7], or [8], wherein the artificial electron mediator as defined in (i) above is a quinone, a phenazine, a viologen, a cytochrome, a thioredoxin, a phenoxazine, a phenothiazine, a ferricyanide, a ferredoxin, ferrocene, a ferrocene derivative, or a metal complex;

the water-insoluble electron mediator as defined in (ii) above is ferrocene, a water-insoluble quinone, a water-insoluble phenazine, a water-insoluble viologen, a water-insoluble thioredoxin, a water-insoluble phenoxazine, a water-insoluble phenothiazine, a water-insoluble ferredoxin, or a water-insoluble ferrocene derivative; or with regard to (iii) above, further, an electron mediator having an oxidoreduction potential of 0.2 V or higher is not comprised.

[10] A method for electrochemical glucose measurement comprising: a step of bringing a sample that may contain glucose, a free-type flavin compound, and a purified FAD-dependent glucose oxidase or purified FAD-dependent glucose dehydrogenase into contact with one another; and a step of measuring the electric current, wherein, with regard to the method:

(i) an artificial electron mediator capable of accepting an electron on its own from an FAD-dependent glucose oxidase or FAD-dependent glucose dehydrogenase is not externally added;

(ii) a water-insoluble electron mediator capable of accepting an electron on its own from an FAD-dependent glucose oxidase or FAD-dependent glucose dehydrogenase is not externally added; and (iii) an electron mediator capable of accepting an electron on its own from an FAD-dependent glucose oxidase or FAD-dependent glucose dehydrogenase and having an oxidoreduction potential of 0.3 V or higher is not externally added.

[11] A method for electric power generation involving the use of a free-type flavin compound as an electron mediator, wherein the method comprises the use of an anode and a cathode; and the method comprises a step of supplying a flavin compound to an anode that is in contact with an electrolyte and supplying a glucose fuel, wherein the anode comprises a purified FAD-dependent glucose dehydrogenase or purified FAD-dependent glucose oxidase, with the proviso that, with regard to the method:

(i) an artificial electron mediator capable of accepting an electron on its own from an FAD-dependent glucose oxidase or FAD-dependent glucose dehydrogenase is not externally added;

(ii) a water-insoluble electron mediator capable of accepting an electron on its own from an FAD-dependent glucose oxidase or FAD-dependent glucose dehydrogenase is not externally added; and (iii) an electron mediator capable of accepting an electron on its own from an FAD-dependent glucose oxidase or FAD-dependent glucose dehydrogenase and having an oxidoreduction potential of 0.3 V or higher is not externally added.

[12] The method according to [10] or [11], wherein the flavin compound is a non-enzymatic flavin compound immobilized on a solid phase.

[13] The method according to any of [10] to [12], wherein the purified FAD-dependent glucose oxidase or purified FAD-dependent glucose dehydrogenase is immobilized on a solid phase.

[14] The method according to any of [10] to [13], wherein the flavin compound is a compound represented by Formula (I):

(I)

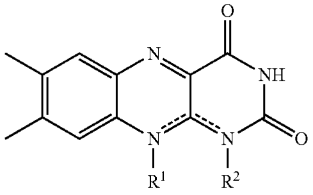

wherein $R^1$ is not present or represents —$CH_3$ or:

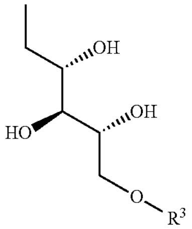

and, when $R^1$ is not present, the nitrogen atom depicted as being bound to $R^1$ forms a double bond with the adjacent carbon atom and $R^2$ represents H, $R^2$ is not present or represents H, and, when $R^2$ is not present, the nitrogen atom depicted as being bound to $R^2$ forms a double bond with the adjacent carbon atom, and $R^3$ represents H, a phosphoric acid group, or:

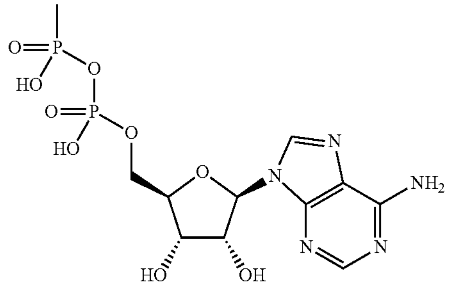 [SMILES: CP(=O)(O)OP(=O)(O)OC[C@H]1O[C@@H](n2cnc3c(N)ncnc32)[C@H](O)[C@@H]1O]

[15] The method according to any of [10] to [14], wherein the flavin compound is flavin mononucleotide, riboflavin, lumichrome, flavin adenine dinucleotide, or lumiflavin.

[16] The method according to any of [10] to [15], wherein the artificial electron mediator as defined in (i) above is a quinone, a phenazine, a viologen, a cytochrome, a thioredoxin, a phenoxazine, a phenothiazine, a ferricyanide, a ferredoxin, ferrocene, a ferrocene derivative, or a metal complex;

the water-insoluble electron mediator as defined in (ii) above is ferrocene, a water-insoluble quinone, a water-insoluble phenazine, a water-insoluble viologen, a water-insoluble thioredoxin, a water-insoluble phenoxazine, a water-insoluble phenothiazine, a water-insoluble ferredoxin, or a water-insoluble ferrocene derivative; or with regard to (iii) above, further, an electron mediator having an oxidoreduction potential of 0.2 V or higher is not added externally.

This description includes the content as disclosed in Japanese Patent Application No. 2016-205539, which is a priority document of the present application.

Advantageous Effects of Invention

Unlike conventional mediators such as potassium ferricyanide, the flavin compound of the present invention is generally present in vivo, highly biocompatible, and considered non-toxic or less-toxic to a human body. Accordingly, a composition comprising the flavin compound of the present invention and the method of measurement involving the use of such flavin compound may be used for self-contained continuous glucose measurement. In addition, the flavin compound of the present invention may be applied to a glucose fuel cell.

Figure 1:
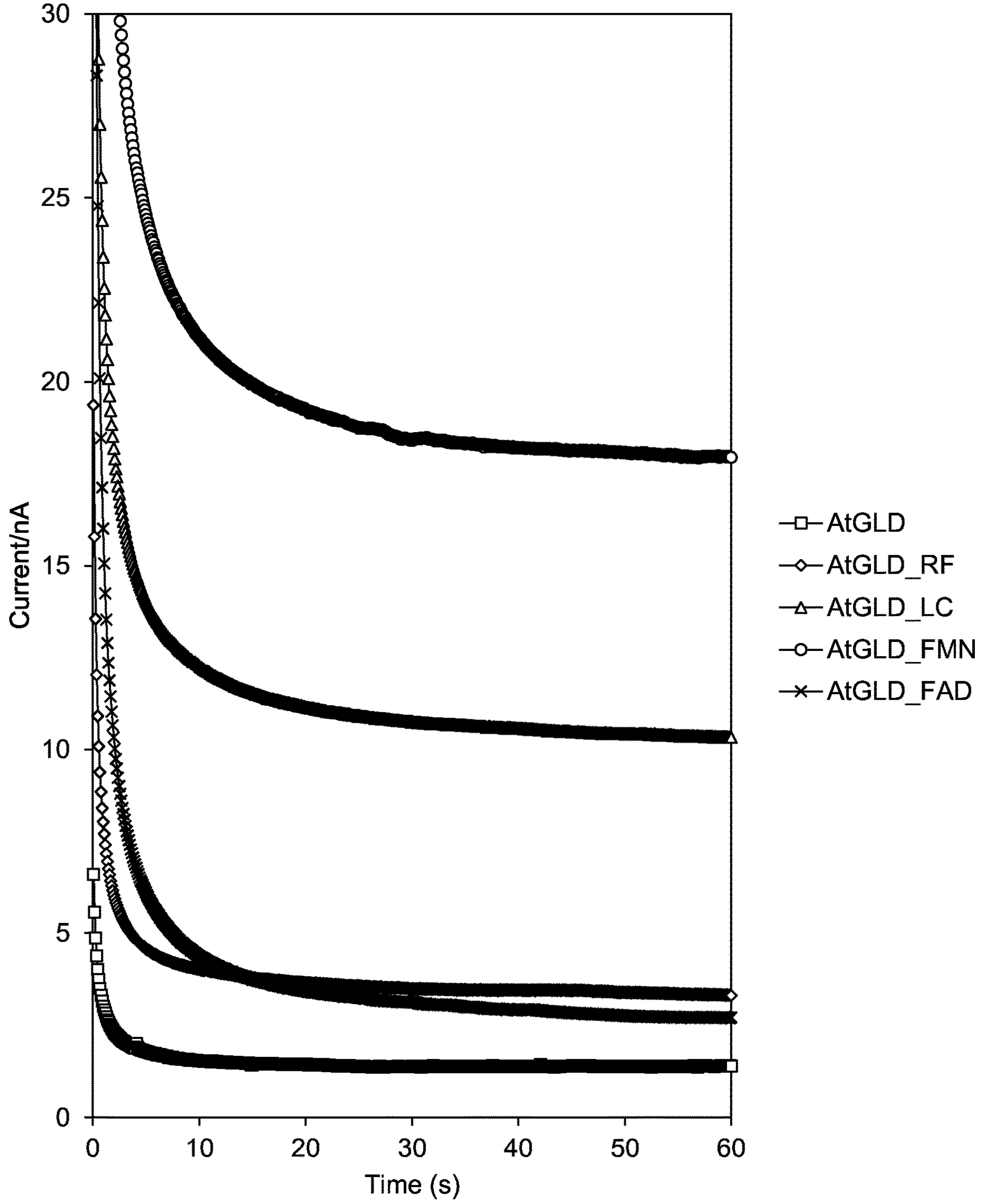
FIG. 1 shows response currents observed when AtGLD and various flavin compounds are used.

DESCRIPTION OF EMBODIMENTS (A Flavin Compound and a Composition Containing a Flavin Compound)

In one embodiment, the present invention provides a flavin compound. In another embodiment, the present invention provides a composition for glucose measurement comprising a flavin compound. The flavin compound of the present invention functions as a mediator in a glucose redox reaction catalyzed by a glucose oxidase or glucose dehydrogenase. The expression (flavin compound) "functions as a mediator" means that the flavin compound is involved in electron transfer and, in a system using an electrode, for example, the flavin compound of the present invention accepts an electron from GOD or GDH and becomes reduced, transfers the electron to an electrode, and then returns to its oxidized form. From this perspective, the flavin compound of the present invention can also be referred to as an electron transfer mediating agent. In the present description, these terms are synonymous with each other.

GODs or GDHs which are FAD-dependent form holoenzymes together with a coenzyme; i.e., the flavin-type compound, FAD. Unless specified otherwise, the term "GOD" used herein refers to FAD-dependent GOD. Unless specified otherwise, the term "GDH" used herein refers to FAD-dependent GDH. In a holoenzyme, FAD is non-covalently bound to the enzyme to form a complex, and is usually embedded in the enzyme. That is, FAD comprised in a holoenzyme is not free in the solution. A GOD or GDH that does not have a coenzyme is referred to as an "apoenzyme," and does not exhibit activity on glucose. The phrase "the flavin compound of the present invention" used herein does not encompass a coenzyme comprised within a holoenzyme. That is, the flavin compound of the present invention exists in a form free from an enzyme. Unless specified otherwise, the term "the flavin compound of the present invention" as used herein refers to a free flavin compound or a free-type flavin compound. As a corollary, a coenzyme FAD contained in a holoenzyme of GOD or GDH does not fall under "the flavin compound of the present invention" as used herein.

Incidentally, in one embodiment, the flavin compound of the present invention may be immobilized on a solid phase, such as an electrode surface, and used. In such case, likewise, the immobilized flavin compound is not comprised in the holoenzyme, and exists independently from the GOD or GDH enzyme. Accordingly, such immobilized flavin compound is also within the scope of the term "free-type flavin compound" used herein for convenience. A flavin compound that exists independently from such GOD or GDH enzyme may also be referred to as a non-enzymatic flavin compound, a non-enzymatically bound flavin compound, or the like. The non-enzymatic flavin compound and non-enzymatically bound flavin compound may also be immobilized on a solid phase.

In one embodiment, the flavin compound of the present invention may be a compound represented by Formula (I):

(I)

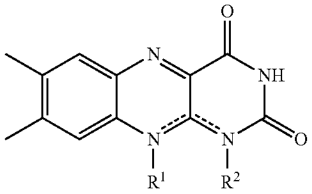

wherein $R^1$ is not present or represents —$CH_3$ or:

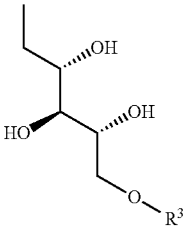

and, when $R^1$ is not present, the nitrogen atom depicted as being bound to $R^1$ forms a double bond with the adjacent carbon atom and $R^2$ represents H;

$R^2$ is not present or represents H, and, when $R^2$ is not present, the nitrogen atom depicted as being bound to $R^2$ forms a double bond with the adjacent carbon atom, and $R^3$ represents H, a phosphoric acid group, or:

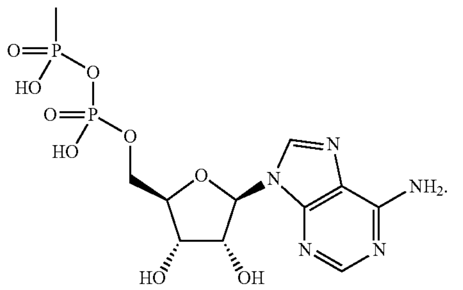 [SMILES: CP(=O)(O)OP(=O)(O)OC[C@H]1O[C@@H](n2cnc3c(N)ncnc32)[C@H](O)[C@@H]1O]

In one embodiment, the flavin compound of the present invention is riboflavin (RF) (CAS 83-88-5).

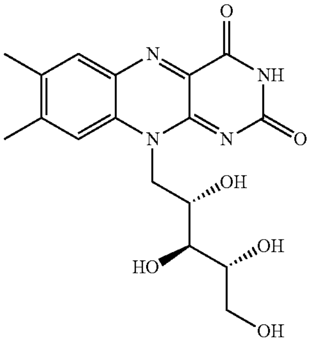 [SMILES: Cc1cc2nc3c(=O)[nH]c(=O)nc-3n(C[C@H](O)[C@H](O)[C@H](O)CO)c2cc1C]

In one embodiment, the flavin compound of the present invention is flavin mononucleotide (FMN) (CAS 146-17-8).

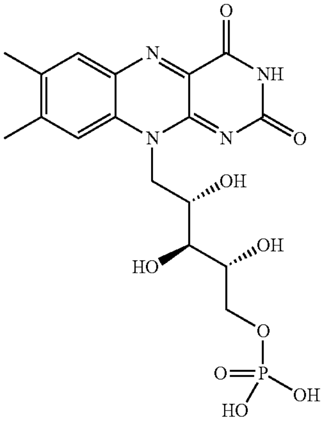 [SMILES: Cc1cc2nc3c(=O)[nH]c(=O)nc-3n(C[C@H](O)[C@H](O)[C@H](O)COP(=O)(O)O)c2cc1C]

In one embodiment, the flavin compound of the present invention is lumichrome (LC) (CAS 1086-80-2).

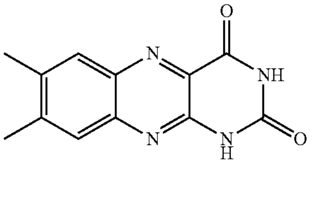 [SMILES: Cc1cc2nc3[nH]c(=O)[nH]c(=O)c3nc2cc1C]

In one embodiment, the flavin compound of the present invention is flavin adenine dinucleotide (FAD) (CAS 146-14-5).

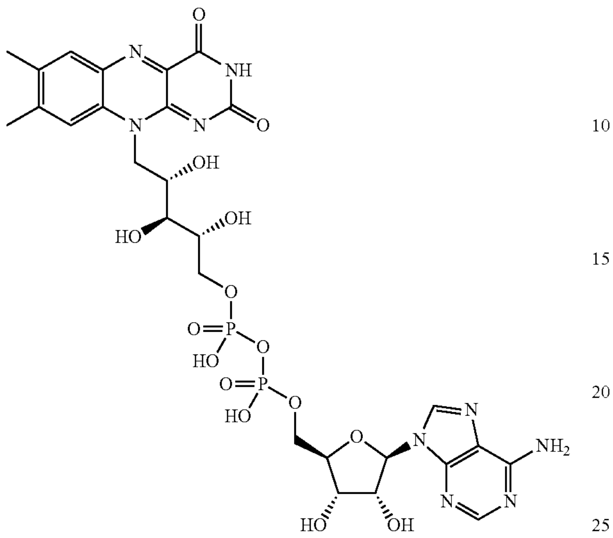

In one embodiment, the flavin compound of the present invention is lumiflavin (LF) (CAS 1088-56-8).

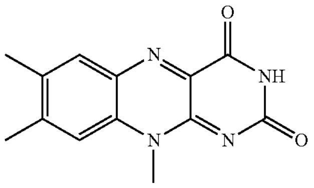 [SMILES: Cc1cc2nc3c(=O)[nH]c(=O)nc-3n(C)c2cc1C]

It is known that flavin compounds, in general, have three different redox states and three different ionized states. In the chemical formulae above, the flavin compounds of the present invention are represented in neutral and oxidized form. However, the flavin compound of the present invention may not only be in these forms, but also in oxidized form (quinone form), semiquinone form, or reduced form (hydroquinone form). Further, the flavin compound of the present invention may be in neutral or anionic form. For convenience of description, the flavin compound of the present invention, such as the flavin compound of the present invention represented by the chemical formula above, encompasses a flavin compound in any of neutral, anionic, oxidized, semiquinone, or reduced form. For example, when a neutral and oxidized compound is added as the flavin compound of the present invention to a system of measurement, for example, such compound may be converted into an oxidized and anionic compound due to the pH level of the solution or proton transfer. Such compound is also encompassed in the scope of the flavin compound of the present invention.

The flavin compound of the present invention may be artificially synthesized or a naturally occurring type may be obtained. Further, a commercially available flavin compound may also be used.

In one embodiment, the flavin compound of the present invention may be used in combination with a glucose dehydrogenase (FAD-dependent GDH). In another embodiment, the flavin compound of the present invention may be used in combination with a glucose oxidase (FAD-dependent GOD). In another embodiment, the composition comprising the flavin compound of the present invention further comprises glucose dehydrogenase or glucose oxidase. GDH or GOD may be free in a solution or may be immobilized on a solid phase. GDH or GOD may exist independently, or may be linked to another compound or protein, such as an enzyme or antibody.

In one embodiment, the composition containing the flavin compound of the present invention:

(i) does not comprise an externally added artificial electron mediator capable of accepting an electron on its own from an FAD-dependent glucose oxidase or FAD-dependent glucose dehydrogenase;

(ii) does not comprise an externally added water-insoluble electron mediator capable of accepting an electron on its own from an FAD-dependent glucose oxidase or FAD-dependent glucose dehydrogenase; or (iii) does not comprise an externally added electron mediator capable of accepting an electron on its own from an FAD-dependent glucose oxidase or FAD-dependent glucose dehydrogenase and having an oxidoreduction potential of 0.3 V or higher. In one embodiment, the same applies to the electrode of the present invention and the sensor of the present invention. Unless specified otherwise, the oxidoreduction potential is described relative to a silver-silver chloride electrode as the reference electrode.

In one embodiment, regarding the method for electrochemical glucose measurement and the method for electric power generation involving the use of the flavin compound of the present invention:

(i) an artificial electron mediator capable of accepting an electron on its own from an FAD-dependent glucose oxidase or FAD-dependent glucose dehydrogenase is not added externally;

(ii) a water-insoluble electron mediator capable of accepting an electron on its own from an FAD-dependent glucose oxidase or FAD-dependent glucose dehydrogenase is not added externally; or (iii) an electron mediator capable of accepting an electron on its own from an FAD-dependent glucose oxidase or FAD-dependent glucose dehydrogenase and having an oxidoreduction potential of 0.3 V or higher is not added externally. Incidentally, added externally as used herein with regard to an electron mediator encompasses addition immediately before the measurement, during the measurement, and during preparation of a measurement reagent.

In one embodiment, the composition, the electrode, and the sensor comprising the flavin compound of the present invention do not comprise an externally added electron mediator that is capable of accepting an electron on its own from an FAD-dependent glucose oxidase or FAD-dependent glucose dehydrogenase and has an oxidoreduction potential of 0.3 V or higher, 0.2 V or higher, 0.1 V or higher, or 0 V or higher to 0.8 V or lower, 0.7 V or lower, or 0.6 V or lower. In another embodiment, the composition, the electrode, and the sensor comprising the flavin compound of the present invention do not comprise an externally added electron mediator that is capable of accepting an electron on its own from an FAD-dependent glucose oxidase or FAD-dependent glucose dehydrogenase and has an oxidoreduction potential of 0 to 0.8 V, 0 to 0.7 V, 0 to 0.6 V, 0.1 to 0.7 V, 0.2 to 0.6 V, 0.3 to 0.8 V, 0.3 to 0.7 V, or 0.3 to 0.6 V. In one embodiment, the method using the flavin compound of the present invention also does not comprise using such electron mediator.

In one embodiment, the composition, the electrode, and the sensor comprising the flavin compound of the present invention do not comprise (include) an externally added water-insoluble electron mediator capable of accepting an electron on its own from an FAD-dependent glucose oxidase or FAD-dependent glucose dehydrogenase. Examples of water-insoluble electron mediators include, but are not limited to, ferrocene, water-insoluble quinones such as phenanthrolinequinone, water-insoluble phenazines such as phenazine, water-insoluble viologens, water-insoluble thioredoxins, water-insoluble phenoxazines, water-insoluble phenothiazines, water-insoluble ferredoxins, and water-insoluble ferrocene derivatives. In one embodiment, with regard to the method using the flavin compound of the present invention, use of such electron mediator is also excluded.

In one embodiment, the composition, the electrode, and the sensor comprising the flavin compound of the present invention do not comprise a conventional artificial electron mediator capable of accepting an electron on its own from an FAD-dependent glucose oxidase or FAD-dependent glucose dehydrogenase. In one embodiment, the method using the flavin compound of the present invention also does not comprise using such electron mediator. Examples of conventional artificial electron mediators capable of accepting an electron on its own from an FAD-dependent glucose oxidase or FAD-dependent glucose dehydrogenase include substances that are artificially and externally added, such as potassium ferricyanide, quinones, anthraquinones, phenazines, viologens, cytochromes, thioredoxins, phenoxazines, phenothiazines, ferricyanides such as potassium ferricyanide, ferredoxins, ferrocene or ferrocene derivatives, and metal complexes such as osmium complexes, cobalt complexes, ruthenium complexes, iron complexes, and vanadium complexes and capable of accepting an electron on its own from an FAD-dependent glucose oxidase or FAD-dependent glucose dehydrogenase. Such compounds and derivatives may comprise one or more functional groups selected from among a sulfonyl group, a sulfo group, a carbonyl group, a carboxyl group, an amino group, an imino group, a nitro group, a nitroso group, a hydroxy group, an alkyl group (e.g., $C_{1-16}$ alkyl, such as methyl), an alkoxyl group, an acyl group, a cyano group, and a halogen group. Specific examples of the electron mediator compound include 1,1'-dimethyl ferrocene, ferrocene carboxylic acid, ferrocene carboxyaldehyde, benzoquinone, hydroquinone, ferricyanide/ferrocyanide (K or Na salt, such as potassium ferricyanide), ferricinium/ferrocene, phenazine methosulfate, 1-methoxy-5-methylphenazinium methyl sulfate, 2,6-dichlorophenolindophenol, chloranil, bromanyl, phenanthrolinequinone, anthraquinone, octacyanotungstate ion, octacyanomolybdate ion, $[Ni(PQ_3)]^{2+}$ ion, such as $Ni(PQ_3)]Cl_2$, $[Ni(PQ)_3]Br_2$, $[Os(dmo)_2(1\text{-vinylimidazole})X]X$, $[Os(dmo)_2(1\text{-vinylimidazole})X]X_2$, $[Os(dmo)_2(\text{imidazole})X]X$, $[Os(dmo)_2(\text{imidazole})X]X_2$, $[Os(dmo)_2(1\text{-methylimidazole})X]X_2$, and $[Os(dmo)_2(\text{methylimidazole})X]X_2$ (in these compounds, "dmo" represents 4,4'-dimethoxy-2,2'-bipyridine and "X" represents halogen), and a compound capable of accepting an electron on its own from an FAD-dependent glucose oxidase or FAD-dependent glucose dehydrogenase.

In one embodiment, an artificial electron mediator capable of accepting an electron on its own from an FAD-dependent glucose oxidase or FAD-dependent glucose dehydrogenase can be, for example, potassium ferricyanide, ferrocene, $[Ni(PQ_3)]Cl_2$, or $[Ni(PQ)_3]Br_2$. In one embodiment, accordingly, the composition, the electrode, and the sensor comprising the flavin compound of the present invention do not comprise potassium ferricyanide, ferrocene, $[Ni(PQ_3)]Cl_2$, or $[Ni(PQ)_3]Br_2$. In one embodiment, in addition, these substances are not added in the method of the present invention.

When the ruthenium complex is used as the sole electron mediator, it is known that FAD-dependent GDH does not accept an electron from the ruthenium complex upon application of a given potential. However, when 1-mPMS is added to the system comprising the ruthenium complex and FAD-dependent GDH, it is known that the ruthenium complex becomes capable of accepting an electron upon application of a given potential (see JP 2013-083634 A). Without wishing to be bound by any specific theory, it is believed that the interaction between the ruthenium complex and FAD-dependent GDH prevents the ruthenium complex from coming into proximity close enough to accept an electron from FAD comprised in the GDH. It is believed that, for this reason, when the ruthenium complex is used as the sole electron mediator in combination with FAD-dependent GDH, a response current is not observed even when a given potential is applied. On the other hand, when another artificial electron mediator, 1-mPMS, capable of accepting an electron on its own directly from FAD-dependent GDH is present in this system, it is believed that 1-mPMS first accepts an electron from then FAD-dependent GDH and then transfer the electron to the ruthenium complex. Here, regarding a system comprising a ruthenium complex as the sole electron mediator and FAD-dependent GDH, the ruthenium complex does not fall under the scope of "the artificial electron mediator capable of accepting an electron on its own from an FAD-dependent glucose oxidase or FAD-dependent glucose dehydrogenase" herein. However, when 1-mPMS is additionally present in the system, the ruthenium complex becomes capable of accepting an electron. As such, in the system comprising 1-mPMS and the ruthenium complex as electron mediators and FAD-dependent GDH, the combination of 1-mPMS and ruthenium complex is capable of accepting an electron from an FAD-dependent glucose oxidase or FAD-dependent glucose dehydrogenase. In such a case, if the flavin compound of the present invention is used instead of 1-mPMS, it is believed that the free-type flavin compound present in the solution will accept an electron from FAD-dependent GDH, and the flavin compound can then transfer the electron to the ruthenium complex. In one embodiment, the present invention encompasses such combination of the electron mediator and the flavin compound of the present invention. That is, in one embodiment, the composition for glucose measurement of the present invention comprises a free-type flavin compound, a purified FAD-dependent glucose oxidase or purified FAD-dependent glucose dehydrogenase, and a ruthenium complex that is not capable of accepting an electron on its own from an FAD-dependent glucose oxidase or FAD-dependent glucose dehydrogenase but is capable of accepting an electron from the flavin compound of the present invention in the presence of the flavin compound of the present invention, such as hexaammineruthenium. Conversely, the present invention does not exclude use of such combination of the electron mediator and the flavin compound of the present invention. As such, while an artificial electron mediator capable of accepting an electron on its own from an FAD-dependent glucose oxidase or FAD-dependent glucose dehydrogenase is excluded from the composition of the present invention, a conventional artificial electron mediator capable of further accepting an electron from the free-type flavin compound of the present invention that had accepted an electron from an FAD-dependent glucose oxidase or FAD-dependent glucose dehydrogenase is not excluded (i.e., such conventional artificial electron mediator is included in the present invention). In other words, the composition of the present invention does not comprise an artificial electron mediator capable of accepting an electron on its own directly from an FAD-dependent glucose oxidase or FAD-dependent glucose dehydrogenase. The same applies to the electrode, the sensor, and the method of the present invention.

Incidentally, with regard to the above, externally adding a mediator to the composition or the measurement system refers to adding the mediator at a concentration that affects the response current in the measurement of glucose concentration (i.e., adding in an amount effective for glucose measurement). For example, even if a very small amount of an artificial electron mediator that does not affect the response current is externally added to the composition of the present invention in the measurement of glucose concentration, such addition does not affect the measurement of glucose concentration carried out using the composition of the present invention and, therefore, a mediator added in such amount is encompassed by the present invention. Further, the phrase the composition of the present invention does not comprise an externally added artificial electron mediator means the composition does not substantially comprise an externally added artificial electron mediator. That is, the composition may contain a very small amount of artificial electron mediator that does not affect the response current, but the composition does not comprise a substantial amount of artificial electron mediator that does affect the response current. As such, in one embodiment, a composition containing a substantial amount of artificial electron mediator capable of accepting an electron on its own from an FAD-dependent glucose oxidase or FAD-dependent glucose dehydrogenase that affects the response current is excluded from the present invention. Further, with regard to the measurement of glucose concentration associated with a human body, even if a very small amount of artificial electron mediator capable of accepting an electron on its own from an FAD-dependent glucose oxidase or FAD-dependent glucose dehydrogenase is externally added to the composition of the present invention in an acceptable amount that does not adversely affect the human body and that does not affect the response current, such mediator will not affect the measurement of glucose concentration carried out using the composition of the present invention and, therefore, externally adding a mediator in such amount is encompassed in the present invention. The same applies to the electrode, the sensor, and the method of the present invention.

The present inventor previously reported a fusion protein composed of FAD-dependent GDH linked to a cytochrome (WO 2017/094776). In WO 2017/094776, the fusion protein is referred to as "Cytb-GDH" or "GDH-Cytb." In one embodiment, such fusion protein may be used as the FAD-dependent GDH. In such a case, the cytochrome moiety comprised in the fusion protein (e.g., Cytb-GDH) is part of the fusion protein, and does not fall under the cytochrome to be externally added as used herein. Accordingly, in one embodiment a composition for glucose measurement comprising a free-type flavin compound and a purified glucose dehydrogenase/cytochrome fusion protein is provided. It should be noted, however, that this composition does not comprise a cytochrome that is externally added.

(Method of Immobilization of GDH or GOD)

GDH or GOD may be immobilized on a solid phase by any known method. For example, GDH or GOD may be immobilized on a bead, membrane, or electrode surface. Examples of immobilization methods include a method of using a crosslinking reagent, a method of embedding in a polymer matrix, a method of covering (coating) with a dialysis membrane, and a method of using a photo-crosslinkable polymer, conductive polymer, or redox polymer and the GDH or GOD may be immobilized in a polymer, immobilized by adsorption onto an electrode, or these means may be used in combination. Typically, GDH or GOD is immobilized onto a carbon electrode using glutaraldehyde, and then treated with a reagent comprising an amine group for blocking of glutaraldehyde. The amount of GDH or GOD to be immobilized can be appropriately determined as the amount necessary to generate an electric current necessary for electrochemical measurement or fuel cell electric power generation.

(Method for Immobilization of the Flavin Compound of the Present Invention)

In one embodiment, the flavin compound of the present invention may be present in a solution alone, or it may be immobilized onto a solid phase such as a bead, membrane, or electrode surface. Examples of immobilization methods include a method of using a crosslinking reagent, a method of embedding in a polymer matrix, a method of covering with a dialysis membrane, and a method of using a photo-crosslinkable polymer, conductive polymer, or redox polymer and the flavin compound may be immobilized in a polymer, immobilized by adsorption onto an electrode, or these means may be used in combination. The amount of the flavin compound to be immobilized can be appropriately determined as the amount necessary to generate an electric current necessary for electrochemical measurement or fuel cell electric power generation.

In one embodiment, the flavin compound of the present invention may be immobilized, and GDH or GOD may further be immobilized. In this case, these substances may be immobilized with the same or different methods.

The final concentration of the flavin compound of the present invention to be added to the sample solution is not particularly limited and, for example, may be 0.01 to 200 mM, 0.02 to 150 mM, 0.03 to 100 mM, 0.04 to 80 mM, 0.05 to 60 mM, 0.06 to 50 mM, 0.08 to 40 mM, 0.1 mM to 30 mM, 0.15 to 20 mM, 0.2 to 10 mM, 0.3 to 5 mM, or 0.4 to 3 mM. The final concentration can be, for example, 0.05 to 10 mM. The final concentration of the flavin compound of the present invention to be added to the sample solution is not particularly limited and, for example, may be 0.001 to 5% (w/v), 0.003 to 3% (w/v), 0.005 to 1% (w/v), 0.01 to 0.5% (w/v), 0.02 to 0.3% (w/v), or 0.03 to 0.1% (w/v). The order of adding the flavin compound and other enzymes or reagents is not limited, and these substances may be added simultaneously or successively.

When the flavin compound is used in combination with GOD, the concentration of the components of a reagent for electrochemical measurement can be adjusted in accordance with a concentration range of a reduced-form mediator contained in the sample or presumed to be generated in the sample.

Unless otherwise specified, a glucose dehydrogenase or glucose oxidase contained in the composition of the present invention is a purified enzyme. Cell extracts, solutions containing disrupted cells, and crude enzyme extracts containing GOD or GDH also contain various contaminants, in addition to GOD and GDH. In the case of microorganisms, for example, the amount of riboflavin in a crude enzyme extract is reported to be about 53 to 133 μM (J. Indust. Micro. Biotech., 1999, 22, pp. 8-18). When such crude enzyme extract or the like per se is subjected to electrochemical measurement, contaminants accept electrons and this hinders electron transmission from and to the electrode and, therefore, at the riboflavin concentration mentioned above, it is difficult to carry out accurate electrochemical measurement in a crude enzyme extract. Therefore, the method of electrochemical glucose measurement of the present invention uses GOD or GDH from which contaminants have been removed (depleted of contaminants). In the present specification, the expression GOD or GDH is purified or is a purified enzyme does not necessarily require the protein to be a pure protein but rather refers to contaminants being removed from the enzyme preparation (the enzyme preparation being depleted of contaminants) to the extent that glucose electrochemical measurement can be carried out.

(Glucose Dehydrogenase)

Glucose dehydrogenases are found throughout nature and can be obtained by searching for enzymes from microorganisms, animals, and plants. In microorganisms, glucose dehydrogenase can be obtained from, for example, filamentous fungi, yeast, or bacteria. The glucose dehydrogenase of the present invention may be a GDH from, for example, a microorganism classified in the subphylum *Mucor*, the class *Mucor*, the order *Mucor*, or the family *Mucor*, for example, species such as the genus *Mucor*, the genus *Absidia*, the genus *Actinomucor*, or the genus *Circinella* or a mutant thereof.

Examples of microorganisms belonging to the genus *Mucor* include *Mucor prainii, Mucor circinelloides, Mucor hiemalis, Mucor subtilissimus, Mucor guilliermondii, Mucor javanicus*, and *Mucor dimorphosporus*. Examples of microorganisms belonging to the genus *Absidia* include *Absidia cylindrospora* and *Absidia hyalospora*. An example of microorganisms belonging to the genus *Actinomucor* is *Actinomucor elegans*. Examples of microorganisms belonging to the genus *Circinella* include *Circinella* simplex, *Circinella* sp., *Circinella angarensis, Circinella chinensis, Circinella lacrymispora, Circinella minor, Circinella mucoroides, Circinella rigida, Circinella umbellata*, and *Circinella muscae*. In one embodiment, the GDH may be from *Aspergillus oryzae*. In one embodiment, the GDH may be the GDH of Product code: GLD1 of BBI Solutions (from *Aspergillus oryzae*). In one embodiment, the GDH may be GDH from *Aspergillus terreus* (JP Patent No. 5,020,070).

(Glucose Oxidase)

Glucose oxidases are found throughout nature and can be obtained by searching for enzymes from microorganisms, animals, and plants. In microorganisms, glucose oxidase can be obtained from, for example, filamentous fungi, yeast, or bacteria. The glucose oxidase of the present invention may be GOD derived from organism species of, for example, the genus *Aspergillus, Penicillium, Apis, Mucor, Fusarium, Streptomyces*, or *Talaromyces* or a modified form thereof. In one embodiment, the GOD may be Catalog No. GLO-201 of Toyobo Co., Ltd. (from *Aspergillus*). The column describing the structure of GLO-201 in the product catalog thereof recites that GLO-201 is a glycoprotein with 2 moles of FAD, which is a holoenzyme.

(GOD or GDH Gene)

In order to obtain a gene encoding GOD or GDH, in general, a common gene cloning method may be employed. For example, chromosomal DNA or mRNA can be extracted from microbial cells or various cells having GOD or GDH productivity by a conventional method, such as a method described in Current Protocols in Molecular Biology (WILEY Interscience, 1989). Further, cDNA can be synthesized using mRNA as the template. Using chromosomal DNA or cDNA thus obtained, a library of chromosomal DNA or cDNA can be prepared.

Subsequently, a method comprising synthesizing a suitable probe DNA based on the amino acid sequence of GOD or GDH and selecting a GDH gene from the chromosomal DNA or cDNA library with the use of the probe DNA may be performed. Alternatively, a suitable primer DNA may be prepared based on the amino acid sequence, DNA containing the gene fragment of interest may be amplified via an appropriate polymerase chain reaction (PCR) method, such as the 5' RACE method and the 3' RACE method, and the resulting DNA fragments may be ligated to each other to obtain DNA containing the full-length GDH gene of interest.

Any known genes encoding GDH may be used. An example is a GDH gene from the genus *Mucor* (described in JP Patent No. 4,648,993). A gene obtained via modification of the gene exemplified above may be used. For example, the modified genes described in WO 2012/169512 and WO 2015/099112 may be used. Alternatively, a mutant resulting from introduction of the mutations T387A/I545T into the GDH from *Mucor prainii* described in JP Patent No. 4,648,993 (also referred to as "MpGDH") may be used. Another example of a gene encoding GDH is a GDH gene from *Aspergillus terreus* (AtGLD) (JP Patent No. 5,020,070).

Any known genes encoding GOD may be used. An example is a GOD gene from the genus *Aspergillus*. The gene may be a modified gene.

Such genes may be ligated to or inserted into various types of vectors, or such genes may be incorporated into the chromosome or genome. When using vectors, genes can be cloned into vectors with the use of commercially available kits, such as the TA Cloning Kit (Invitrogen) or the In-Fusion HD Cloning Kit (Clontech), commercially available plasmid vector DNA, such as pUC119 (Takara Bio Inc.), pUC18 (Takara Bio Inc.), pBR322 (Takara Bio Inc.), pBluescript SK+(Stratagene), or pYES2/CT (Invitrogen), or commercially available bacteriophage vector DNA, such as XEMBL3 (Stratagene). Using the recombinant DNA, a host organism, such as *Escherichia coli*, preferably the *Escherichia coli* JM109 strain (Takara Bio Inc.) or the *Escherichia coli* DH5α strain (Takara Bio Inc.), is transformed. Recombinant DNA contained in the resulting transformant is purified using, for example, the QIAGEN Plasmid Mini Kit (Qiagen).

(Production of GOD or GDH)

The GOD or GDH may be produced by culturing the transformed cells obtained in the manner described above, allowing the GOD or GDH genes contained in the cells to express, and isolating the expressed protein from the culture product.

In culturing, a medium generally used for culturing filamentous fungi; that is, a medium containing a carbon source, a nitrogen source, inorganic material, and other nutrients at a suitable proportion can be used, and a synthetic or naturally-occurring medium may be used. As the medium for culturing the above microbial host cells, for example, a culture medium prepared by appropriately adding one or more inorganic salts, such as sodium chloride, monopotassium phosphate, dipotassium phosphate, magnesium sulfate, magnesium chloride, ferric chloride, ferric sulfate, or manganese sulfate, and, if necessary, a sugar source, vitamins, and the like to one or more nitrogen sources, such as yeast extract, tryptone, peptone, meat extract, corn steep liquor, or soy or wheat bran steep liquor, is used.

Culture conditions for filamentous fungi generally known to those skilled in the art can be employed and can be appropriately designed. For example, the initial pH level of the medium can be adjusted to 5 to 10, the culture temperature can be 20° C. to 40° C., and the culture duration can be from several hours to several days, preferably 1 to 7 days, and more preferably 2 to 5 days. The culture means is not particularly limited and, for example, aeration stirring submerged culture, shake culture, or static culture can be employed; however, culture is preferably performed under conditions in which a sufficient dissolved oxygen level is maintained. An example of a medium and conditions for culturing microorganisms of the genus *Aspergillus* is shake culture performed using a DPY medium at 30° C. and 160 rpm for 3 to 5 days, as described in the Examples provided below. When culturing microbial host cells, culture may be performed at 10° C. to 42° C., preferably at about 25° C., for 4 to 24 hours, and more preferably at about 25° C. for 4 to 8 hours by means of, for example, aeration stirring submerged culture, shake culture, or static culture.

After the completion of culture, GOD or GDH is collected from the culture. This can be carried out by a conventional enzyme collecting means. For example, the supernatant of the culture is collected, or a fungus body is subjected to ultrasonication disruption treatment or grinding treatment in accordance with a conventional technique, the enzyme is extracted using a lytic enzyme such as lysozyme and the like, or the fungus body is shaken or allowed to stand in the presence of toluene to cause lysis, and the enzyme is thus discharged from the fungus body. Subsequently, the solution is filtered or centrifuged to remove solid matter, and if necessary, nucleic acids are removed using streptomycin sulfate, protamine sulfate, or manganese sulfate and then, ammonium sulfate, an alcohol, acetone, or the like is added thereto, the mixture is fractionated, and the precipitate is collected to obtain a crude enzyme of GOD or GDH.

The crude enzyme may be further purified by any means known in the art. A purified enzyme preparation may be obtained by a method appropriately selected from, for example, gel filtration using Sephadex, ultrogel, or bio gel, adsorption elution using an ion exchanger, electrophoresis using polyacrylamide gel or the like, adsorption elution using hydroxyapatite, sedimentation such as sucrose density gradient centrifugation, hydrophobic chromatography, affinity chromatography, and fractionation using a molecular sieve membrane or hollow fiber membrane or two or more of such methods may be performed in combination to obtain a purified GDH enzyme preparation.

Polyacrylamide gel electrophoresis and staining may be performed to determine whether or not the enzyme is purified. Alternatively, whether or not the enzyme is purified can be determined by testing whether or not glucose electrochemical measurement can be appropriately performed using a glucose sample of known concentration.

(Measurement of GDH Activity)

GDH (EC 1.1.99.10) catalyzes the reaction of oxidizing a hydroxyl group of glucose to generate glucono-6-lactone. In this reaction, an electron acceptor accepts an electron and is converted into a reduced electron acceptor. GDH activity can be measured based on this principle of action using, for example, the following measurement system involving the use of phenazine methosulfate (PMS) and 2,6-dichloroindophenol (DCIP) as electron acceptors.

D-glucose+PMS (oxidized)→D-glucono-δ-lactone+PMS (reduced) (Reaction 1)

PMS (reduced)+DCIP (oxidized)→PMS (oxidized)+DCIP (reduced) (Reaction 2)

Specifically, first, in (Reaction 1), as oxidation of D-glucose proceeds, PMS (reduced) is generated. Then, in subsequent (Reaction 2), as oxidation of PMS (reduced) proceeds, DCIP is reduced. The degree of dissipation of "DCIP (oxidized)" is detected as a change in absorbance at 600 nm, and enzyme activity can be determined based on this change.

GDH activity can be measured in accordance with the following procedure. A 100 mM phosphate buffer (2.05 ml, pH 7.0), 0.6 ml of a 1 M D-glucose solution, and 0.15 ml of a 2 mM DCIP solution are mixed and heated at 37° C. for 5 minutes. Subsequently, 0.1 ml of a 15 mM PMS solution and 0.1 ml of an enzyme sample solution are added to the mixture to initiate the reaction. The absorbance is measured at the time of initiation of the reaction and over time. A decrease in the absorbance at 600 nm per minute as the enzymatic reaction proceeds (ΔA600) is determined, and GDH activity is calculated in accordance with the following equation. Here, 1 U of GDH activity is defined as the amount of the enzyme required for reducing 1 μmol of DCIP at 37° C. in the presence of 200 mM D-glucose per minute.

$$GDH\ \text{activity}(U/\text{mL}) = \frac{-(\Delta A600 - \Delta A600_{blank}) \times 3.0 \times df}{16.3 \times 0.1 \times 1.0}$$

Incidentally, in the equation shown above, the numerical value 3.0 represents the amount (ml) of liquid (reaction reagent+enzyme reagent), the numerical value 16.3 represents the millimolar molecular absorption coefficient ($cm^2$/μmol) under this activity measurement condition, the numerical value 0.1 represents the amount of the enzyme solution (ml), the numerical value 1.0 represents the optical path length of the cell (cm), $\Delta A600_{blank}$ represents the decrease in the absorbance at 600 nm per minute when the reaction is initiated with the addition of a 100 mM phosphate buffer (pH 7.0) instead of the enzyme sample solution; and df represents the dilution factor.

(Measurement of GOD Activity)

GOD (EC 1.1.3.4) catalyzes the reaction of oxidizing a hydroxyl group of glucose to generate glucono-δ-lactone and hydrogen peroxide.

GOD activity can be measured based on this principle of action by allowing the generated hydrogen peroxide to react with peroxidase and allowing a coloration agent to develop color.

Method for Measurement of Glucose Oxidase Activity

<Reagent>

100 mM MES-Na buffer (pH 5.7)

0.5% 4-aminoantipyrine (4AA, Tokyo Chemical Industry Co., Ltd.) solution 5.0 g/l TOOS (N-ethyl-N-(2-hydroxy-3-sulfopropyl)-m-toluidine sodium, Dojindo Laboratories) solution 400 U/ml peroxidase (POD, Kikkoman Corporation) solution 1.2 M D-glucose solution The MES-Na buffer (30.0 ml), the 4AA solution (0.3 ml), the TOOS solution (0.3 ml), the POD solution (0.3 ml), and the D-glucose solution (6.0 ml) are mixed to prepare a reaction reagent.

<Measurement Conditions>

The reaction reagent (3 ml) is preheated at 37° C. for 5 minutes. The GOD solution (0.1 ml) is added, the mixture is moderately mixed, and then the absorbance at 555 nm is measured using a spectrophotometer regulated at 37° C. with water as the control. The measurement value is defined as a change in the absorbance at 555 nm per minute from 1 minute after the initiation of measurement to that 3 minutes after the initiation of measurement. The number of micromoles of hydrogen peroxide generated per minute at 37° C. is designated as the active unit (U) in an enzyme solution, and this is calculated according to the following equation.

$$\text{Activity(U/ml)}=\{(\Delta As-\Delta A0)\times 3.1\times df\}/(32.8\times 0.5\times 0.1)$$

ΔAs: change in the absorbance of the reaction solution per minute

ΔA0: change in the absorbance of the control solution per minute 32.8: the millimolar absorption coefficient of quinoneimine dye generated by the reaction (mM-1 $cm^{-1}$)

0.5: the number of moles of quinoneimine dye generated by 1 mol of hydrogen peroxide df: the dilution factor (Glucose Assay Kit)

In one embodiment, the present invention provides a glucose assay kit comprising the flavin compound of the present invention. In one embodiment, this kit comprises GDH. In another embodiment, this kit comprises GOD. Use of this kit enables an assay of glucose in the blood (blood glucose level) using GOD or GDH. Measurement may be carried out continuously.

The glucose assay kit of the present invention comprises the flavin compound of the present invention at an amount sufficient for at least one assay. Typically, the glucose assay kit of the present invention comprises, in addition to the flavin compound of the present invention, GOD or GDH, a buffer necessary for the assay, a glucose standard solution for preparing a calibration curve, and instructions. In one embodiment, the glucose assay kit of the present invention, such as the glucose assay kit for SMBG, CGM, or FGM, comprises the flavin compound of the present invention and GOD or GDH in the form of a single reagent. In another embodiment, the glucose assay kit of the present invention comprises the flavin compound and GOD or GDH in the form of different reagents. The flavin compound of the present invention may be provided in various forms, such as a freeze dried reagent, a reagent immobilized onto a bead or an electrode surface, or a solution stored in a proper preservation solution. Preferably, the compound may be provided in the form of a solution stored in a light-shielded container.

Glucose concentration can be measured, for example, in the manner described below when a colorimetric glucose assay kit is used. The glucose assay kit comprises, in the reaction layer thereof, a liquid- or solid-state composition containing GDH and one or more substance selected from the group consisting of N-(2-acetamide)imide diacetate (ADA), bis(2-hydroxyethyl)iminotris(hydroxymethyl)methane (Bis-Tris), sodium carbonate, and imidazole as a reaction accelerating agent. A pH buffer and a coloration reagent (allochroic reagent, i.e., color changing reagent) are added, where necessary. To this is added a sample containing glucose, and the reaction is allowed to proceed for a given period of time. During this time period, the absorbance corresponding to the maximum absorption wavelength of the dye polymerized and generated by directly accepting an electron from the GDH or the reduced dye is monitored. When a rate method is employed, the glucose concentration in the sample can be calculated based on the rate of change in the absorbance per time unit. When an endpoint method is employed, the glucose concentration can be computed based on a change in the absorbance up to the time point at which glucose in the sample is entirely oxidized with reference to a calibration curve prepared in advance using glucose solutions of standard concentrations.

Coloration reagents (allochroic reagents) that can be used in this method includes, for example, 2,6-dichloroindophenol (DCIP). This may be added as an electron acceptor and the decrease of the absorbance at 600 nm may be monitored to perform glucose quantification. Further, nitrotetrazolium blue (NTB) may be added as the coloration reagent, the amount of generated diformazan may be determined by measuring the absorbance at 570 nm, and glucose concentration can be thus calculated. It should be noted the coloration reagent (allochroic reagent) to be used is not limited thereto.

(Glucose Sensor)

In one embodiment, the present invention provides a glucose sensor involving the use of the flavin compound of the present invention. The glucose sensor of the present invention comprises the flavin compound of the present invention and GDH or GOD. As the electrode of the glucose sensor, a carbon electrode, a gold electrode, a platinum electrode, or the like can be used, and GOD or GDH enzyme may be applied or immobilized onto the electrode. In addition thereto or independently therefrom, the flavin compound of the present invention may be applied or immobilized onto the electrode. With regard to methods of immobilization, see the section on "Method of immobilization of GDH or GOD" above.

The flavin compound of the present invention and GOD or GDH may be applied to various electrochemical measurement methods using a potentiostat, a galvanostat, and the like. Examples of electrochemical measurement methods include amperometry, voltammetry such as cyclic voltammetry, potentiometry, and coulometry. For example, the electric current upon glucose reduction may be measured by amperometry to determine the glucose concentration in the sample. The voltage to be applied varies depending on the conditions and setting of the apparatus and may be, for example, −1000 mV to +1000 mV (vs. Ag/AgCl).

(Electrochemical Measurement of Glucose)

In one embodiment, the present invention provides a method for electrochemical measurement of glucose comprising: a step of bringing a sample that may contain glucose, a free-type flavin compound, and a purified glucose oxidase or purified glucose dehydrogenase into contact with one another; and a step of measuring the electric current. Such flavin compound and/or enzyme may be immobilized onto a solid phase.

Electrochemical measurement of glucose concentration may be performed, for example, in the manner described below. Add a buffer to a constant-temperature cell, and hold the temperature at a constant level. Use an electrode onto which GDH or GOD is immobilized as the working electrode, as well as a counter electrode (e.g., a platinum electrode) and a reference electrode (e.g., an Ag/AgCl electrode or an Ag/Ag+ electrode). Add the flavin compound of the present invention to the reaction solution. Apply a constant voltage to the carbon electrode, add a sample containing glucose after the electric current becomes stationary, and measure an increase in the electric current. Based on the calibration curve prepared using glucose solutions of standard concentrations, the glucose concentration in the sample can be calculated. The voltage to be applied may be, for example, +800 mV or lower, +700 mV or lower, +600 mV or lower, +500 mV or lower, +400 mV or lower, +300 mV or lower, +200 mV or lower, +100 mV or lower, or +50 mV or lower to −200 mV or higher, −100 mV or higher, −50 mV or higher, or 0 mV or higher. For example, it can be +800 mV to −200 mV, +800 mV to −100 mV, +800 mV to −50 mV, +600 mV to 0 mV, +500 mV to 0 mV, +400 mV to 0 mV, +300 mV to 0 mV, or +200 mV to 0 mV (with reference to a silver-silver chloride reference electrode).

More specifically, 0.2 U to 150 U, and preferably 0.5 U to 100 U of GDH or GOD is immobilized onto a glassy carbon (GC) electrode, and the response current value corresponding to the glucose concentration is measured. A 100 mM potassium phosphate buffer (10.0 ml, pH 6.0) is added to an electrolytic cell. A GC electrode is connected to a potentiostat BAS100B/W (manufactured by BAS), the solution is stirred at 37° C., and a voltage of +500 mV is then applied with reference to a silver-silver chloride reference electrode. To this system, a 1 M D-glucose solution is added to result in a final concentration of 5, 10, 20, 30, 40, or 50 mM, and the current value at a stationary state is measured for each addition. The current values are plotted relative to known glucose concentrations (5, 10, 20, 30, 40, and 50 mM) to produce a calibration curve. Thus, glucose quantification may be performed with an electrode to which GDH or GOD has been immobilized.

In addition, a printed electrode can also be used for the electrochemical measurement. This can reduce the amount of solution required for the measurement. In this case, it is preferable that the electrode be provided on an insulating substrate. More specifically, it is desirable that the electrode be provided on a substrate by means of a printing technique, such as photolithography, screen printing, gravure printing, or flexography. Examples of materials for the insulating substrate include silicon, glass, ceramic, polyvinyl chloride, polyethylene, polypropylene, and polyester, and use of a material having high resistance to various solvents and chemical agents is preferable. The area of a working electrode can be determined depending on the response current of interest. In one embodiment, for example, the area of the working electrode can be 1 $mm^2$ or larger, 1.5 $mm^2$ or larger, 2 $mm^2$ or larger, 2.5 $mm^2$ or larger, 3 $mm^2$ or larger, 4 $mm^2$ or larger, 5 $mm^2$ or larger, 6 $mm^2$ or larger, 7 $mm^2$ or larger, 8 $mm^2$ or larger, 9 $mm^2$ or larger, 10 $mm^2$ or larger, 12 $mm^2$ or larger, 15 $mm^2$ or larger, 20 $mm^2$ or larger, 30 $mm^2$ or larger, 40 $mm^2$ or larger, 50 $mm^2$ or larger, 1 $cm^2$ or larger, 2 $cm^2$ or larger, 3 $cm^2$ or larger, 4 $cm^2$ or larger, 5 $cm^2$ or larger, or 10 $cm^2$ or larger. In another embodiment, the area of the working electrode can be 10 $cm^2$ or smaller, 5 $cm^2$ or smaller, or 1 $cm^2$ or smaller. The same applies to the counter electrode.

In one embodiment, an apparatus for continuous glucose measurement comprising the glucose sensor of the present invention is provided. The apparatus for continuous glucose measurement may comprise a continuous glucose monitoring (CGM) device or flash glucose monitoring (FGM) device that enables monitoring of changes in blood glucose levels for 24 hours. In another embodiment, the present invention provides a method for continuous glucose monitoring involving the use of the composition, electrode, or sensor of the present invention.

In one embodiment, the CGM device of the present invention may comprise a glucose sensor to be placed subcutaneously. The sensor can be mounted for a given period of time, such as 1 day to 3 weeks. The sensor may be disposable or reusable. The sensor may comprise a sensor membrane layer to prevent direct contact between tissue and the enzyme. The sensor may be designed to be inserted into the abdominal region using an applicator. In one embodiment, the present invention provides a CGM device, which further comprises a transmitter and a connector from the sensor to the transmitter. The transmitter need not be implanted. Preferably, the transmitter is capable of communicating with a radio-wave receiver. The CGM device may further comprise an electrical receiver that continuously displays glucose levels. Optionally, the CGM device may comprise finger sticks (i.e., finger stick members) for calibration. The CGM device may contain instructions for use.

(The Fuel Cell of the Present Invention)

In one embodiment, the present invention provides an anode for a fuel cell comprising the flavin compound of the present invention or a composition containing a flavin compound and a fuel cell comprising said anode. In another embodiment, the present invention provides a method for electric power generation (method for generating electric power) comprising using the flavin compound of the present invention, a composition containing a flavin compound, or the anode and glucose as a fuel.

The fuel cell of the present invention comprises the flavin compound of the present invention, a fuel tank, a cathode, an anode comprising GOD or GDH, and an electrolyte. The fuel cell of the present invention may comprise a resistor (load resistor) between the anode and the cathode, according to need, and wiring wire thereof. In one embodiment, the resistor constitutes a part of the fuel cell of the present invention. In another embodiment, the resistor is not part of the fuel cell of the present invention, while the fuel cell of the present invention is configured to be connectable to an appropriate resistor. In the fuel cell of the present invention, the GOD or GDH constitutes part of the anode. For example, the GOD or GDH may be located in the vicinity of the anode or may be in contact therewith, may be immobilized thereon, or may be adsorbed thereto. The fuel tank comprises glucose. That is, the term "fuel cell" used herein refers to a fuel cell using glucose as the fuel, unless specified otherwise. By the action of GOD or GDH, glucose is oxidized, a reduced-form mediator is generated, the mediator transfers an electron to the electrode, and then an electric current flows. In one embodiment, the fuel cell of the present invention may comprise an ion-exchange membrane that separates the anode from the cathode. The ion-exchange membrane can have pores of 1 nm to 20 nm. The anode can be a general electrode, such as a carbon electrode. For example, an electrode composed of a conductive carbonaceous substance, such as carbon black, graphite, or active carbon, or an electrode composed of a metal, such as gold or platinum, can be used. Specific examples thereof include carbon paper, glassy carbon, and HOPG (highly oriented pyrolytic graphite). As a counter cathode, for example, an electrode composed of an electrode catalyst generally used in a fuel cell, such as platinum or platinum alloy, supported on a conductor composed of a carbonaceous material, such as carbon black, graphite, or active carbon, gold, or platinum or a conductor composed of an electrode catalyst, such as platinum or platinum alloy, may be used as the cathode electrode, and an oxidant (a substrate at the cathode side, e.g., oxygen) is then supplied to the electrode catalyst.

In another embodiment, a substrate-reducing enzyme electrode can be used as the counter cathode of the anode consisting of the substrate-oxidizing enzyme electrode as above. Examples of oxidoreductases which reduce the oxidant include known enzymes, such as laccase and bilirubin oxidase. When an oxidoreductase is used as the catalyst that reduces an oxidant, a known electron-transfer mediator may be used, according to need. The cathode mediator may be the same as or different from the anode mediator. Examples of oxidants include oxygen and hydrogen peroxide.

In one embodiment, an oxygen selective membrane (e.g., a dimethylpolysiloxane membrane) may be placed in the vicinity of the cathode electrode, so as to avoid the influence of impurities (ascorbic acid or uric acid and the like) that interfere with the electrode reaction at the cathode.

The method for electric power generation of the present invention comprises a step of supplying glucose serving as the fuel to the anode comprising GOD or GDH. When glucose is supplied to the anode comprising GOD or GDH, glucose is oxidized and converted into D-glucono-6-lactone, GOD or GDH transfers the simultaneously generated electron to an electron-transfer mediator that mediates electron transfer between the oxidase and the electrode, such as a flavin compound, and the electron-transfer mediator transfers the electron to the conductive substrate (i.e., an anode electrode). When the electron from the anode electrode reaches the cathode electrode through a wiring (external circuit), an electric current is generated.

Proton ($H^+$) generated in the process described above migrates to the cathode electrode in the electrolytic solution. At the cathode electrode, reactions take place between a proton migrating from the anode in the electrolytic solution, an electron migrating from the anode through the external circuit, and an oxidant such as oxygen or hydrogen peroxide (e.g., a cathode substrate), and water is generated. Electric power can be generated utilizing this process.

The flavin compound of the present invention and the composition containing the flavin compound can be used for measurement of glucose concentration in a sample and this can be utilized for diagnosis of diabetes, self-monitoring of blood glucose level, and other purposes. The composition of the present invention can be used in combination with an enzyme electrode, and can be used for various types of electrochemical measurements. Further, the composition of the present invention can be used in combination with an enzyme sensor. In addition, the composition of the present invention can be used for a kit for glucose measurement as well as a glucose sensor. Further, the flavin compound of the present invention and the composition containing the flavin compound can be used for a fuel cell. That is, the flavin compound of the present invention and the composition containing the flavin compound can be used for a method of electric power generation using glucose as the fuel. It should be noted that the applications mentioned above are provided for illustrative purposes and that application of the flavin compound of the present invention or the composition containing the flavin compound are not limited thereto.

The present invention will be further illustrated with reference to the examples provided below. However, the technical scope of the present invention is not restricted to these examples in any way.

EXAMPLES

Example 1

1. Introduction of the GDH Gene Derived from the Genus *Mucor* into a Host and Confirmation of GDH Activity First, each of the mutations of T387A/I545T was introduced into the GDH from the genus *Mucor* described in JP Patent No. 4,648,993 (MpGDH) and a gene encoding the GDH mutant was obtained. The amino acid sequence of the MpGDH mutant is shown in SEQ ID NO: 1, and the nucleotide sequence of the gene thereof is shown in SEQ ID NO: 2. The target gene, i.e., the MpGDH mutant gene, was inserted into the multiple cloning site of the plasmid pUC19 using conventional techniques to produce a DNA construct. Specifically, the pUC19 linearized vector provided in the In-Fusion HD Cloning Kit (Clontech) was used as pUC19. At the in-fusion cloning site located in the multiple cloning site of pUC19, the MpGDH mutant gene was ligated using the In-Fusion HD Cloning Kit according to the instructions included in the kit and a plasmid for producing constructs (the pUC19-MpGDH mutant) was obtained.

Further, each of the mutations of N66Y/N68G/C88A/Q233R/T387C/E554D/L557V/S559K was introduced into the GDH from the genus *Mucor* (MpGDH, SEQ ID NO: 1) and a gene encoding the modified GDH (MpGDH-M1) was obtained. The amino acid sequence of MpGDH-M1 is shown in SEQ ID NO: 3, and the nucleotide sequence of the gene thereof is shown in SEQ ID NO: 4. The target gene, i.e., the MpGDH-M1 gene, was inserted into the multiple cloning site of the plasmid pUC19 using conventional techniques to produce a DNA construct. In the same manner as described above, the MpGDH-M1 gene was ligated to the in-fusion cloning site located in the multiple cloning site of pUC19 using the In-Fusion HD Cloning Kit according to the instructions included in the kit and a plasmid for producing construct (pUC19-MpGDH-M1) was obtained.

Using the resulting recombinant plasmid (pUC19-MpGDH-M1) as the template, along with the synthetic oligonucleotides shown in SEQ ID NOs: 7 to 12, and KOD-Plus-(Toyobo Co., Ltd.), PCR was performed under the following conditions.

That is, 5 μl of 10×KOD-Plus-buffer, 5 μl of a dNTPs mixture in which each dNTP was adjusted at 2 mM, 2 μl of a 25 mM $MgSO_4$ solution, 50 ng of the DNA construct comprising the template MpGDH-M1 gene ligated thereto, 15 pmol each of the synthetic oligonucleotides, and 1 unit of KOD-Plus were mixed, and sterilized water was added thereto in order to set the total amount of the solution as 50 μl. The prepared reaction solution was subjected to incubation using a thermal cycler (manufactured by Eppendorf Co.) at 94° C. for 2 minutes, and then a cycle of 94° C. for 15 seconds, 50° C. for 30 seconds, and 68° C. for 6 minutes was repeated 30 times.

A part of the reaction solution was subjected to electrophoresis on 1.0% agarose gel, and specific amplification of a DNA of about 8,000 bp was confirmed. The DNA obtained in this manner was treated with restriction enzyme DpnI (manufactured by New England Biolabs), the remaining template DNA was cleaved, strains of *E. coli* JM109 were transformed, and the transformants were then spread on LB-amp agar media. The grown colonies were inoculated into 2.5 ml of LB-amp media (1% (W/V) bactotrypton, 0.5% (W/V) peptone, 0.5% (W/V) NaCl, 50 μg/ml ampicillin) and subjected to shake culture at 37° C. for 20 hours to obtain a culture product. The culture product was centrifuged at 7,000 rpm for 5 minutes and cells were collected. Subsequently, the recombinant plasmid was extracted and purified from the cells using QIAGEN tip-100 (Qiagen) to obtain 2.5 μg of DNA. The nucleotide sequence of the DNA encoding MpGDH-M1 in the plasmid was determined using a multi-capillary DNA analysis system (Applied Biosystems 3130xl Genetic Analyzer; Life Technologies). As a result, a DNA construct encoding MpGDH-M1/A175C/N214C/G466D (SEQ ID NO: 5), which is a mutant resulting from substitution of alanine at position 175 with cysteine, asparagine at position 214 with cysteine, and glycine at position 466 with aspartic acid, respectively, in the amino acid sequence of SEQ ID NO: 1 was obtained (pUC19-MpGDH-M2) (SEQ ID NO: 6).

These genes were expressed in *Aspergillus sojae* and GDH activity thereof was evaluated.

In order to obtain the MpGDH mutant and MpGDH-M2, specifically, double-joint PCR (Fungal Genetics and Biology, Vol. 41, p. 973-981, 2004) was carried out using the GDH gene to construct a cassette consisting of the 5' arm region—the PyrG gene (uracil auxotrophic marker)—the TEF1 promoter gene—the flavin-binding type GDH gene—the 3' arm region, and the resulting cassette was used to transform the *Aspergillus sojae* NBRC4239-derived pyrG-deficient strain (a strain deficient in 48 bp upstream, 896 bp of coding region, and 240 bp downstream of the pyrG gene). To 100 ml of a polypeptone dextrin liquid medium comprising 20 mM uridine in a 500-ml triangular flask, conidia of the pyrG-deficient strain from *Aspergillus sojae* NBRC4239 were inoculated and subjected to shake culture at 30° C. for about 20 hours, and fungus bodies were then collected. A protoplast was prepared from the fungus bodies collected. Using the resulting protoplast and 20 μg of the DNA construct comprising the target gene inserted therein, transformation was carried out with the protoplast PEG method. Subsequently, incubation was carried out using Czapek-Dox minimal medium (Difco; pH 6) containing 0.5% (w/v) agar and 1.2 M sorbitol at 30° C. for at least 5 days to obtain transformed *Aspergillus sojae* having colony forming ability.

The resulting transformed *Aspergillus sojae* is capable of growing on uridine-free medium as a result of introduction of the pyrG gene, which complements uridine auxotrophy. Strains comprising the target gene introduced thereinto could thus be selected. From among the resulting strains, a transformant of interest was confirmed with PCR and selected.

Each GDH was produced using *Aspergillus sojae* transformants transformed with a MpGDH mutant gene.

To 40 ml of DPY liquid medium (1% (w/v) polypeptone, 2% (w/v) dextrin, 0.5% (w/v) yeast extract, 0.5% (w/v) $KH_2PO_4$, 0.05% (w/v) $MgSO_4 \cdot 7H_2O$; pH not adjusted) in a 200-ml Erlenmeyer flask, conidia of each strain were inoculated and subjected to shake culture at 160 rpm and 30° C. for 4 days. Subsequently, the fungus body was removed by filtration from the culture product, the resulting supernatant fraction of the medium was concentrated to 10 ml using Amicon Ultra-15, 30K NMWL (manufactured by Millipore), the concentrate was applied to HiLoad 26/60 Superdex 200 pg (manufactured by GE healthcare) equilibrated with a 20 mM potassium phosphate buffer (pH 6.5) containing 150 mM NaCl and eluted with the same buffer. Fractions exhibiting GDH activity were collected to obtain purified products of the MpGDH mutant and MpGDH-M2. Incidentally, this enzyme is bound to FAD at the FAD-binding site thereof (holoenzyme).

2. Introduction of the GDH Gene from *Aspergillus terreus* into a Host and Obtaining a Purified Sample The GDH gene from *Aspergillus terreus* described in JP Patent No. 5,020,070 (AtGLD) was expressed in *Aspergillus sojae* in the same manner as described above. In addition, GDH was produced in the same manner as described above, and the supernatant fraction of the media was purified to obtain a purified AtGLD product. This enzyme is bound to FAD at the FAD-binding site thereof (holoenzyme).

3. Evaluation of a Sensor Using a Flavin-Type Compound

Using a purified product of the MpGDH mutant and two types of flavin compounds (i.e., riboflavin (RF) and flavin mononucleotide (FMN)), chronoamperometry was carried out using a printed electrode. Specifically, 10 μl of a solution comprising a purified MpGDH mutant enzyme at 35 mg/ml was applied onto a DEP chip electrode (equipped with a circular carbon dam ring; manufactured by BioDevice Technology) having a glassy carbon working electrode (2.64 $mm^2$) and a silver-silver chloride reference electrode printed thereon. Thereafter, the DEP chip electrode was connected to the ALS electrochemical analyzer 814D (manufactured by BAS) using a DEP chip specific connector. Chronoamperometry was then carried out with the application of a voltage of +300 mV (vs. $Ag/Ag^+$). Specifically, a potassium phosphate buffer (final concentration: 50 mM, pH 7.0) and 10 μl of a solution containing 20 mM glucose and 100 μM RF were placed on the electrode, the reaction was allowed to proceed, and the current value was measured for 60 seconds. Another measurement was carried out in the same manner, except that 1 mM FMN was used instead of 100 μM RF. As a control, the same test was carried out using a glucose solution containing no RF or FMN.

Figure 4:
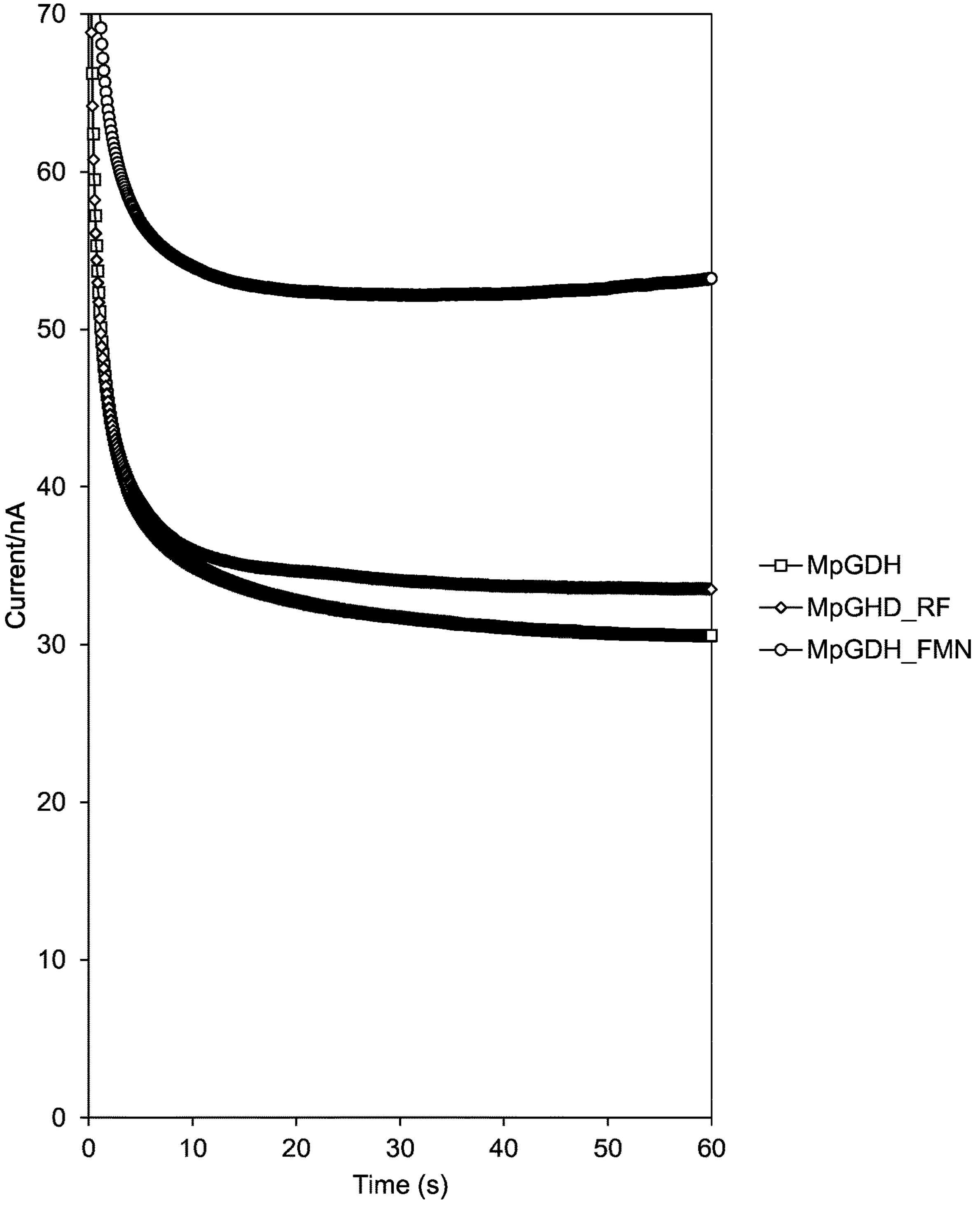
FIG. 4 shows response currents observed when MpGDH and various flavin compounds are used.

The results are shown in FIG. 4. FIG. 4 shows the results of chronoamperometry of the MpGDH mutant enzyme mixed with RF or FMN. A significantly higher response current was observed with the addition of RF or FMN, compared with the case without the addition of RF or FMN. When RF or FMN was not added, the response current was 30.6 nA with the application of a voltage of +300 mV (vs. $Ag/Ag^+$) 60 seconds after the initiation of measurement, 33.5 nA when RF was added, and as high as 53.2 nA when FMN was added.

Subsequently, the purified product of GDH-M2 was used to carried out measurement in the same manner as described above. As a result, a significantly higher response current was observed with the addition of RF or FMN, compared with the case without the addition of RF or FMN. When RF or FMN was not added, the response current was 17.5 nA with the application of a voltage of +300 mV (vs. $Ag/Ag^+$) 60 seconds after the initiation of measurement, 19.2 nA when RF was added, and as high as 19.6 nA when FMN was added. That is, compared with the background, measurable response currents were observed.

Using the purified product of AtGLD and four types of flavin compounds (i.e., RF, FMN, lumichrome (LC), and flavin adenine dinucleotide (FAD)), subsequently, chronoamperometry was carried out using a printed electrode in the same manner as described above, except that a voltage of +100 mV (vs. $Ag/Ag^+$) was applied and 100 μM RF, 1 mM FMN, 100 μM LC, and 1 mM FAD were used. The results are shown in FIG. 1. FIG. 1 shows the results of chronoamperometry of the AtGLD enzyme and RF, FMN, LC, or FAD. A significantly higher response current was observed with the addition of RF or FMN, LC, and FAD, compared with the case without the addition of the flavin compound. When the flavin compound was not added, the response current was 1.4 nA with the application of a voltage of +100 mV (vs. $Ag/Ag^+$) 60 seconds after the initiation of measurement, 3.3 nA when RF was added, 17.9 nA when FMN was added, 10.3 nA when LC was added, and as high as 2.7 nA when FAD was added. That is, compared with the background, a measurable response current was observed. When the flavin compound was added without the addition of glucose, the response current was lower than 1.4 nA in each case.

Figure 2:
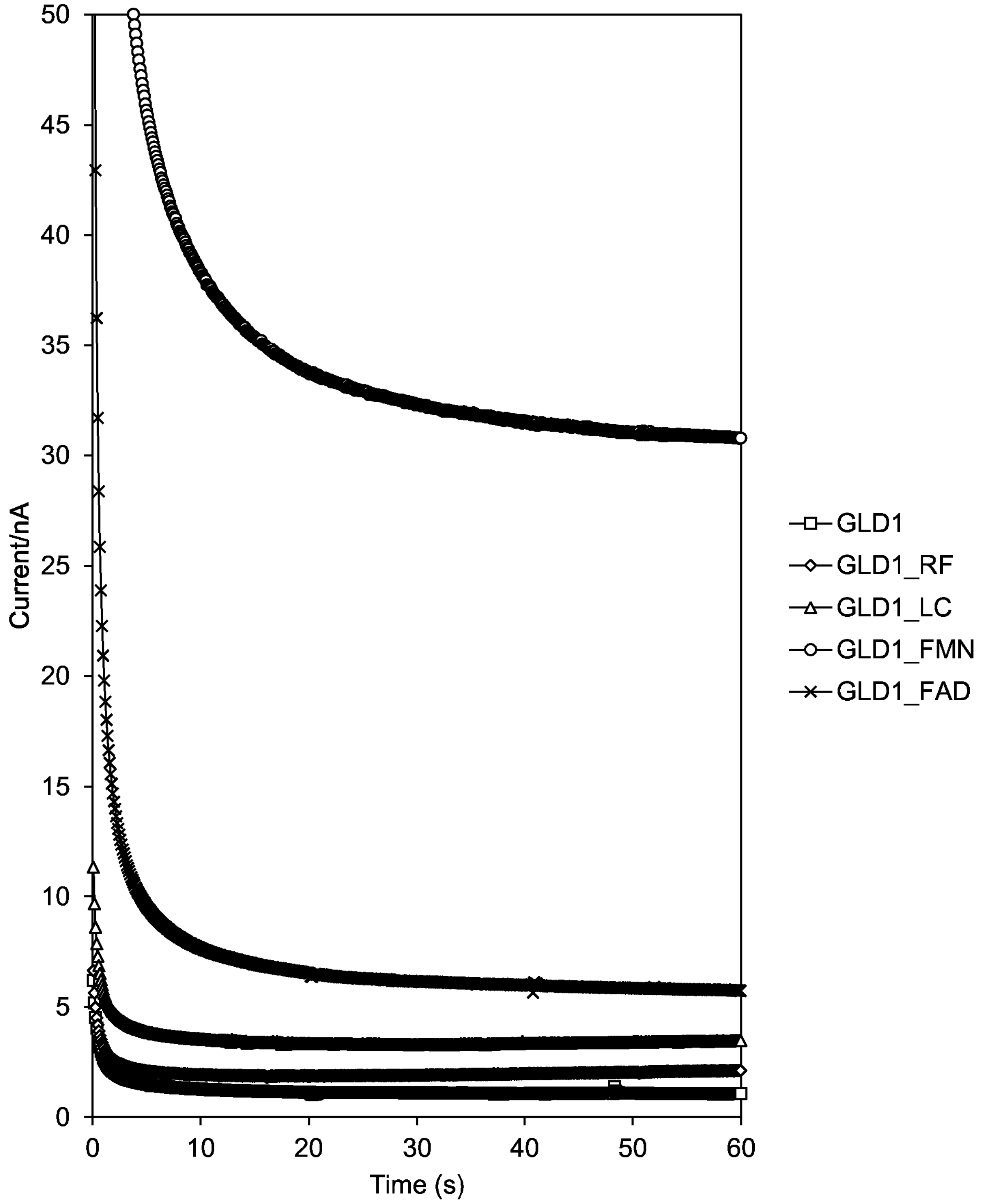
FIG. 2 shows response currents observed when GLD1 and various flavin compounds are used.

Subsequently, using glucose dehydrogenase (FAD-dependent) (manufactured by BBI, Product Code: GLD1, hereafter referred to as "GLD1") and four types of flavin compounds (i.e., RF, FMN, LC, and FAD), chronoamperometry was carried out using a printed electrode in the same manner as described above. Incidentally, this GDH was also bound to FAD via its FAD-binding site (holoenzyme). In this case, however, a voltage of +100 mV (vs. $Ag/Ag^+$) was applied. The results are shown in FIG. 2. FIG. 2 shows the results of chronoamperometry of the GLD1 enzyme mixed with RF, FMN, LC, or FAD. A significantly higher response current was observed with the addition of RF or FMN, LC, and FAD, compared with the case without the addition of the flavin compound. When the flavin compound was not added, the response current was 1.1 nA with the application of a voltage of +100 mV (vs. $Ag/Ag^+$) 60 seconds after the initiation of measurement, 2.1 nA when RF was added, 30.8 nA when FMN was added, 3.5 nA when LC was added, and as high as 5.7 nA when FAD was added. That is. compared with the background, measurable response currents were observed.

Figure 3:
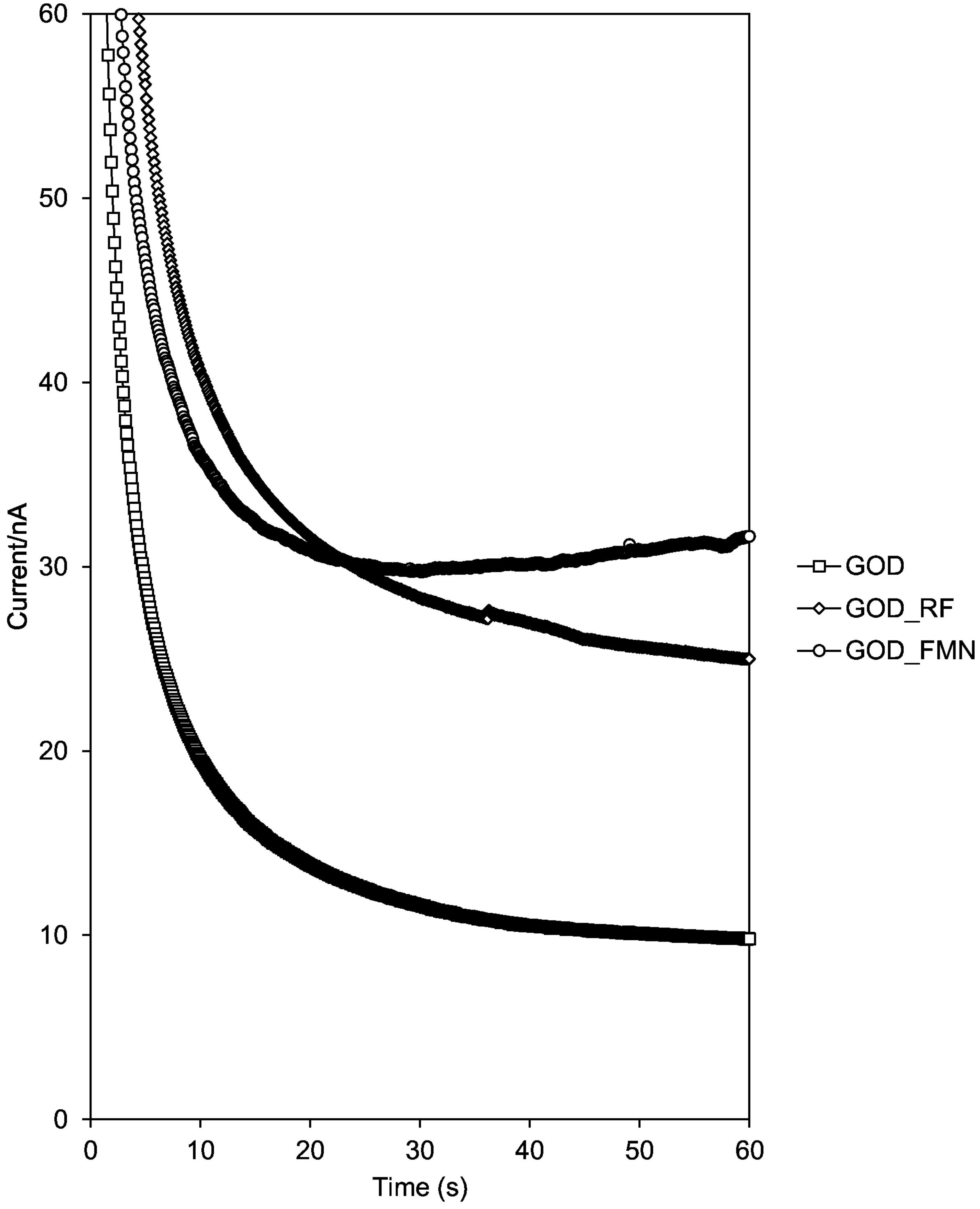
FIG. 3 shows response currents observed when GOD and various flavin compounds are used.

Subsequently, using glucose oxidase (manufactured by Toyobo Co., Ltd., Product Code: GLO-201, hereafter referred to as "GOD") and two types of flavin compounds (i.e., RF and FMN), subsequently, chronoamperometry was carried out using a printed electrode in the same manner as described above. This GOD is also bound to FAD via its FAD-binding site (holoenzyme). In this case, Screen-Printed Electrodes (manufactured by Drop Sense, DRP-110) comprising a carbon working electrode (12.6 $mm^2$) as a printed electrode and a silver reference electrode printed thereon were used and connected to the ALS electrochemical analyzer 814D (manufactured by BAS) using a specific connector (manufactured by Drop Sense, DRP-CAC). A voltage of +100 mV (vs. $Ag/Ag^+$) was applied. The results are shown in FIG. 3. FIG. 3 shows the results of chronoamperometry of the GOD enzyme mixed with RF or FMN. A significantly higher response current was observed with the addition of RF or FMN, compared with the case without the addition of the flavin compound. When RF or FMN was not added, the response current was 9.8 nA with the application of a voltage of +100 mV (vs. $Ag/Ag^+$) 60 seconds after the initiation of measurement, 25.0 nA when RF was added, and as high as 31.6 nA when FMN was added. That is, compared with the background, measurable response currents were observed.

As described above, use of a flavin-type compound lead to an increase in the response current observed upon a reaction between GDH or GOD and glucose and glucose could be measured with high sensitivity. In addition, the response current depends on glucose concentration and, therefore, a response current based on a sample containing glucose at a known concentration can be measured in advance to prepare a calibration curve, the response current of a sample containing glucose at unknown concentration can be measured, and glucose concentration can be measured based on the calibration curve. Incidentally, it should be noted that the above examples are provided merely for illustrative purposes and the present invention is not limited thereto. For example, when a higher response current is preferable, the electrode area, such as the area of a working electrode, can be increased.

As a result the above observation(s), an increased response current was observed in the presence of the flavin compound of the present invention, compared with the case in the absence of the flavin compound. It was thus demonstrated that the free-type flavin compound of the present invention functions as a mediator and mediates electron transfer when GOD or GDH oxidizes glucose into gluconolactone. The oxidoreduction potentials of the flavin compounds are known and it is known that electron transfer is possible depending on the oxidoreduction potential of the counterpart compound. To date, however, there has been no report with regard to actual measurement of glucose carried out by mixing a flavin compound with GDH or GOD.

Example 2

Confirmation of Glucose Concentration Dependence in Electrochemical Measurement

2 µl of a 35 mg/ml GLD1 solution, 3 µl of a 20 mM potassium phosphate buffer (pH 7.0) containing 1.5 M potassium chloride, and 5 µl of 1 mM FMN were mixed, and the resulting mixture was applied on a DEP chip electrode. Cyclic voltammetry was then carried out by sweeping the voltage from −400 mV to +200 mV (vs. Ag/AgCl). The voltage sweep rate was 10 mV/sec. Subsequently, a 2 M glucose solution was added to adjust glucose concentration at various levels, and cyclic voltammetry was carried out in the same manner. The oxidation current ($I_O$) and the reduction current ($I_R$) measured at particular potentials were summed, the resulting value was divided by 2, and whether or not the determined value would increase in a glucose-concentration-dependent manner was examined. In chronoamperometry in which a particular potential of a voltage is applied, in general, if the value of the stable response current increases in a substrate concentration-dependent manner, then it is known that the $(I_O+I_R)/2$ value at the same potential as described above in the cyclic voltammetry also increases, i.e., these two values correlate.

Figure 5:
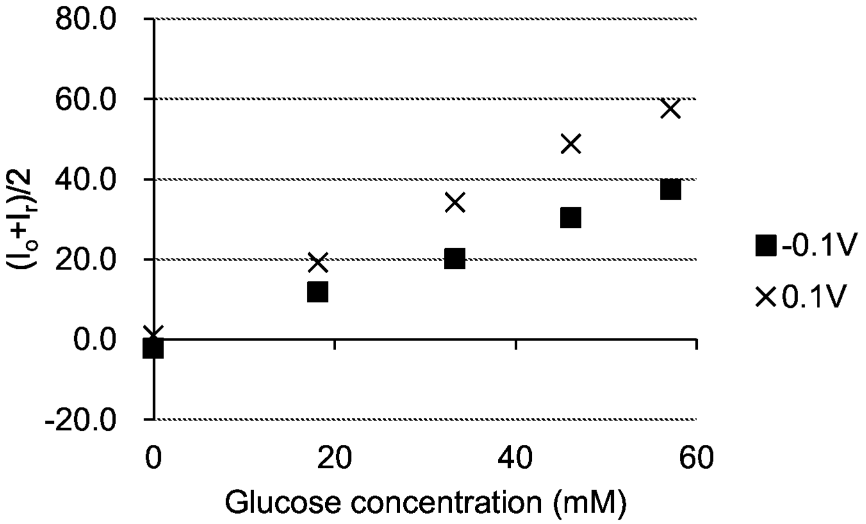
FIG. 5 shows response currents of samples containing glucose at different concentrations observed when GLD1 and FMN are used.

FIG. 5 shows the results of measurement carried out by mixing GLD1 and FMN and plotting glucose concentration against the $(I_O+I_R)/2$ value. As a result, an increase was observed in the $(I_O+I_R)/2$ value at +100 mV (vs. Ag/AgCl) in a glucose concentration-dependent manner, and FMN was found to function as a mediator. In addition, an increase was observed in the $(I_O+I_R)/2$ value at −100 mV (vs. Ag/AgCl) in a glucose concentration-dependent manner.

It is believed that a response current will not be observed when the measurement is carried out under the same conditions using a conventional artificial electron mediator instead of the flavin compound of the present invention for the following reasons. That is, a conventional artificial electron mediator has an oxidoreduction potential different from that of the flavin compound of the present invention and, for example, the oxidoreduction potential of potassium ferricyanide is around 250 mV. As such, even if potassium ferricyanide is used as a mediator, a response current will not be observed with the application of a voltage of merely about 100 mV, and a voltage of at least about 350 mV shall be necessary in order to observe a response current. However, when the compound of the present invention was used, a response current was observed even at a potential as low as +100 mV. This is advantageous for various applications.

Figure 6:
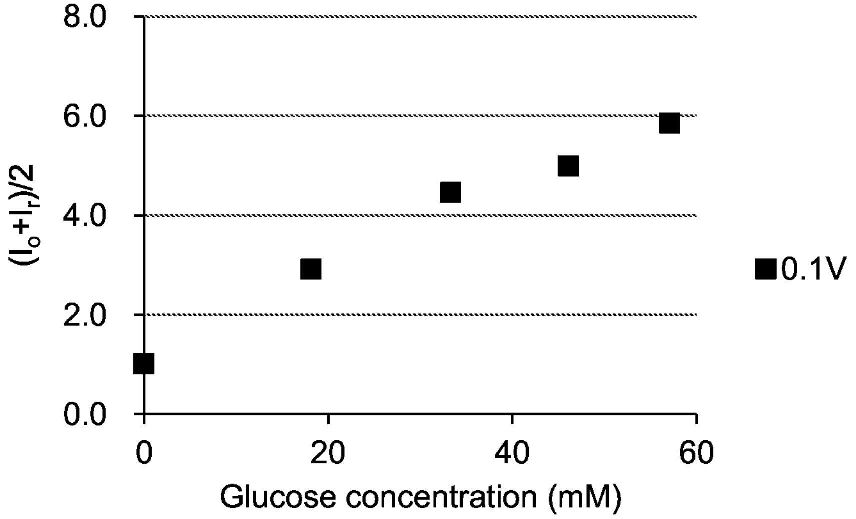
FIG. 6 shows response currents of samples containing glucose at different concentrations observed when GDH-M2 and FMN are used.

Subsequently, MpGDH-M2 was mixed with FMN in the same manner as described above, and the resulting mixture was then subjected to cyclic voltammetry by sweeping the voltage from −400 mV to +200 mV (vs. Ag/AgCl). FIG. 6 shows the results of plotting glucose concentration against the $(I_O+I_R)/2$ value. As a result, an increase was observed in the $(I_O+I_R)/2$ value at +100 mV (vs. Ag/AgCl) in a glucose concentration-dependent manner, and FMN was found to function as a mediator.

Figure 7:
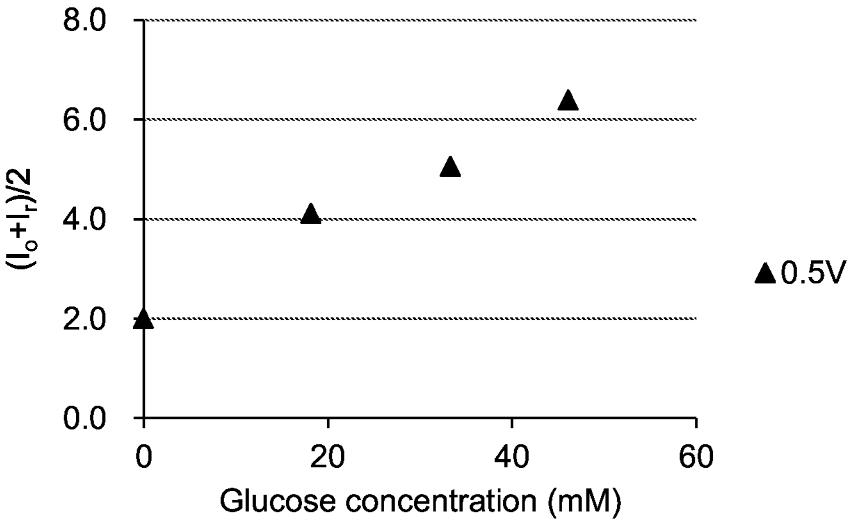
FIG. 7 shows response currents of samples containing glucose at different concentrations observed when GLD1 and FAD are used.

Subsequently, 2 µl of a 35 mg/ml GLD1 solution, 3 µl of a 20 mM potassium phosphate buffer (pH 7.0) containing 1.5 M potassium chloride, and 5 µl of 1 mM FAD were mixed, and the resulting mixture was mounted on a DEP chip electrode. Cyclic voltammetry was then carried out by sweeping the voltage over a range of from 0 mV to +600 mV (vs. Ag/AgCl). The voltage sweep rate was 10 mV/sec. Subsequently, a 2 M glucose solution was added to adjust glucose concentration at various levels, and cyclic voltammetry was carried out in the same manner. FIG. 7 shows the results of measurement carried out by mixing GLD1 and FAD and plotting glucose concentration against the $(I_O+I_R)/2$ value. As a result, an increase was observed in the $(I_O+I_R)/2$ value at +100 mV (vs. Ag/AgCl) in a glucose concentration-dependent manner, and FAD was found to function as a mediator.

Figure 8:
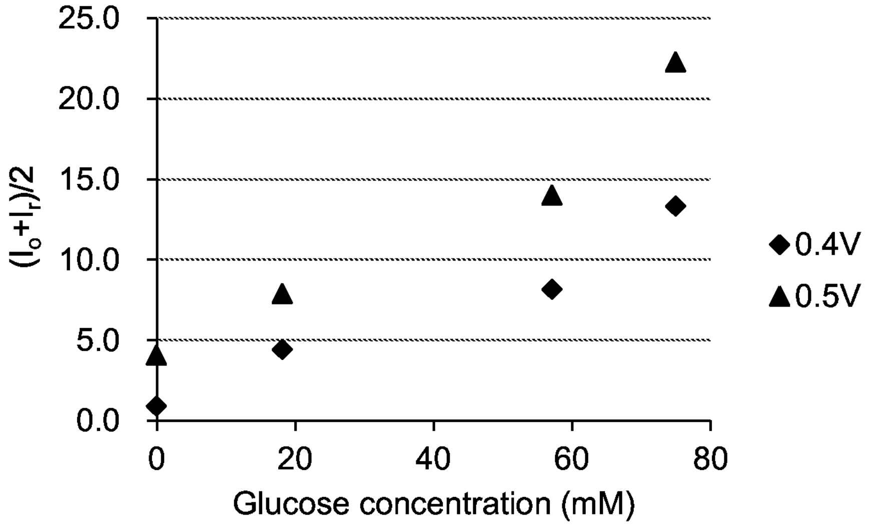
FIG. 8 shows response currents of samples containing glucose at different concentrations observed when GDH-M2 and RF are used.

Subsequently, 2 μl of a 35 mg/ml MpGD-M2 solution, 3 μl of a 20 mM potassium phosphate buffer (pH 7.0) containing 1.5 M potassium chloride, and 5 μl of 100 μM RF were mixed, and the resulting mixture was mounted on a DEP chip electrode. Cyclic voltammetry was then carried out by sweeping the voltage over a range of from 0 mV to +600 mV (vs. Ag/AgCl). The voltage sweep rate was 10 mV/sec. Subsequently, a 2 M glucose solution was added to adjust glucose concentration at various levels, and cyclic voltammetry was carried out in the same manner. FIG. 8 shows the results of measurement carried out by mixing MpGDH-M2 and RF and plotting glucose concentration against the $(I_O+I_R)/2$ value. As a result, an increase was observed in the $(I_O+I_R)/2$ value at +500 mV (vs. Ag/AgCl) in a glucose concentration-dependent manner, and FAD was found to function as a mediator. In addition, glucose concentration dependence was also confirmed at +400 mV (vs. Ag/AgCl).

Figure 9:
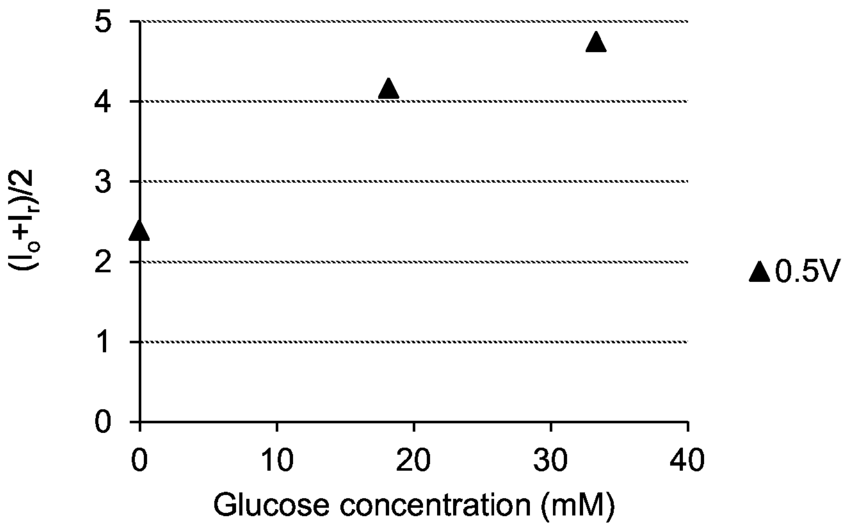
FIG. 9 shows response currents of samples containing glucose at different concentrations observed when GLD1 and LC are used.

Subsequently, 2 μl of a 35 mg/ml GLD1 solution, 3 μl of a 20 mM potassium phosphate buffer (pH 7.0) containing 1.5 M potassium chloride, and 5 μl of 100 μM LC were mixed, and the resulting mixture was mounted on a DEP chip electrode. Cyclic voltammetry was then carried out by sweeping the voltage over a range of from 0 mV to +600 mV (vs. Ag/AgCl). The voltage sweep rate was 10 mV/sec. Subsequently, a 2 M glucose solution was added to adjust glucose concentration at various levels, and cyclic voltammetry was carried out in the same manner. FIG. 9 shows the results of measurement carried out by mixing GLD1 and LC and plotting glucose concentration against the $(I_O+I_R)/2$ value. As a result, an increase was observed in the $(I_O+I_R)/2$ value at +500 mV (vs. Ag/AgCl) in a glucose concentration-dependent manner, and LC was found to function as a mediator.

In addition, the effects attained when a ruthenium complex was used in combination with FMN were examined. A 35 mg/ml GLD1 solution (2 μl), 3 μl of a 20 mM potassium phosphate buffer (pH 7.0) containing 1.5 M potassium chloride, 2.5 μl of 100 μM hexaammineruthenium, and 2.5 μl of 1 mM FMN were mixed, and the resulting mixture was mounted on a DEP chip electrode. Cyclic voltammetry was then carried out by sweeping the voltage over a range of from −400 mV to +200 mV (vs. Ag/AgCl). The voltage sweep rate was 10 mV/sec. Subsequently, a 2 M glucose solution was added to adjust glucose concentration at 18 mM, and cyclic voltammetry was carried out in the same manner. For comparison, hexaammineruthenium only and FMN only were independently tested at the same concentration. As a result of the measurement carried out by mixing GLD1 and hexaammineruthenium with the addition of 18 mM glucose, the $(I_O+I_R)/2$ value was 2 nA at 0 V. The $(I_O+I_R)/2$ value measured by mixing GLD1 and FMN with the addition of 18 mM glucose was 3 nA, and the $(I_O+I_R)/2$ value when the measurement was carried out by mixing GLD1, hexaammineruthenium, and FMN with the addition of 18 mM glucose was 11 nA and, therefore, a synergistic increase in the response current was observed. Incidentally, the $(I_O+I_R)/2$ value was within the range of 0 to 1 nA without the addition of glucose for each case.

Incidentally, if the sensitivity (of the measurement) is several nA, then, glucose can be sufficiently detected using an apparatus for electrochemical measurement and, therefore, by carrying out the measurement described above and by preparing a calibration curve, glucose contained in a sample can be detected with regard to a sample that may contain glucose at an unknown concentration. As such, when the response current is slightly increased with the addition of glucose in Example 1 compared with the response current in the absence of glucose, it is understood that the response current can be improved when further adding glucose.

Example 3

1. Fuel Cell Construction

Purified GDH is immobilized on a carbon electrode via cross linking using glutaraldehyde to prepare an anode electrode. Further, bilirubin oxidase (BOD, Amano Enzyme Inc.) is immobilized on a porous carbon electrode to prepare a cathode electrode. A nafion membrane is inserted between the anode electrode and cathode electrode as a solid polymer electrolytic membrane to construct a biofuel cell. Further, on the wiring that connects the anode electrode to the cathode electrode, a resistor of a given load and a voltmeter are inserted in series and in parallel, respectively. To the anode side (of the fuel cell), an electrolytic solution comprising 1 M potassium phosphate buffer (pH 7.0), 10 mM FMN, and 400 mM D-glucose is introduced, glucose is supplied, and the system is allowed to function at 30° C. and pH 7, such that an electric current may flow.

Without wishing to be bound by any specific theory, the fuel cell of the present invention is considered as follows. That is, in Example 1, even when a potential as low as 100 mV was applied, a response current was observed in the presence of the compound of the present invention. As such, with the use of a fuel cell using oxygen, for example, a large electromotive force determined by subtracting 100 mV from the oxidoreduction potential of oxygen is expected. This is advantageous for various applications.

INDUSTRIAL APPLICABILITY

By using the flavin compound of the present invention or the composition containing the flavin compound of the present invention, glucose measurement can be carried out using a less-toxic or non-toxic mediator. These can be used, for example, in a self-contained device for continuous glucose measurement. In addition, these can be used for a glucose fuel cell.

All publications, patents, and patent applications cited herein are incorporated herein by reference in their entirety.

BRIEF DESCRIPTION OF SEQUENCES

SEQ ID NO: 1: the amino acid sequence of *Mucor prainii*-derived GDH

SEQ ID NO: 2: the nucleic acid sequence of *Mucor prainii*-derived GDH

SEQ ID NO: 3: MpGDH-M1 (aa)SEQ ID NO: 4: MpGDH-M1 (DNA)SEQ ID NO: 5: MpGDH-M2 (aa) SEQ ID NO: 6: MpGDH-M2 (DNA)SEQ ID NOs: 7 to 12: Primers All publications, patents, and patent applications cited herein are incorporated herein by reference in their entirety.

The invention claimed is:

1. A method for electrochemical measurement of glucose in a sample, the method comprising:

providing a free-type flavin compound consisting of flavin mononucleotide, lumichrome, flavin adenine dinucleotide, or lumiflavin, bringing the sample comprising glucose, in contact with the free-type flavin compound, and a purified flavin adenine dinucleotide (FAD)-dependent glucose oxidase or a purified FAD-dependent glucose dehydrogenase to provide a measurement system and carrying out an electric current measurement on said measurement system by bringing said measurement system into contact with an electrode, wherein with regard to the method:

(i) an artificial electron mediator capable of accepting an electron on its own from the purified FAD-dependent glucose oxidase or the purified FAD-dependent glucose dehydrogenase is not externally added to said measurement system; and (ii) a water-insoluble electron mediator capable of accepting an electron on its own from the purified FAD-dependent glucose oxidase or the purified FAD-dependent glucose dehydrogenase is not externally added to said measurement system; and further, an electron mediator capable of accepting an electron on its own from the purified FAD-dependent glucose oxidase or the purified FAD-dependent glucose dehydrogenase and having an oxidoreduction potential of 0.2 V or higher is not externally added to said measurement system;

wherein the free-type flavin compound is present in the sample in free form and is separate from the purified FAD-dependent glucose oxidase or the purified FAD-dependent glucose dehydrogenase, wherein the purified FAD-dependent glucose oxidase is a holoenzyme or the purified FAD-dependent glucose dehydrogenase is a holoenzyme, and wherein, in the presence of glucose, the free-type flavin compound accepts an electron from the purified FAD-dependent glucose oxidase or the purified FAD-dependent glucose dehydrogenase thereby becoming reduced, and then transfers the electron to the electrode whereby the free-type flavin compound returns to an oxidized form.

2. The method according to claim 1, wherein the purified FAD-dependent glucose oxidase or the purified FAD-dependent glucose dehydrogenase is immobilized on a solid phase.

3. The method according to claim 1, wherein the artificial electron mediator that is not externally added to said measurement system is a quinone, a phenazine, a viologen, a cytochrome, a thioredoxin, a phenoxazine, a phenothiazine, a ferricyanide, a ferredoxin, ferrocene, a ferrocene derivative, or a metal complex; or the water-insoluble electron mediator that is not externally added to said measurement system is ferrocene, a water-insoluble quinone, a water-insoluble phenazine, a water-insoluble viologen, a water-insoluble thioredoxin, a water-insoluble phenoxazine, a water-insoluble phenothiazine, a water-insoluble ferredoxin, or a water-insoluble ferrocene derivative.

4. The method of claim 1, further comprising the step of applying a voltage to the sample to determine the presence of glucose.

5. The method according to claim 1, wherein the free-type flavin compound has an oxidoreduction potential that is higher than an oxidoreduction potential of a FAD molecule within the purified FAD-dependent glucose oxidase or within the purified FAD-dependent glucose dehydrogenase.

6. A method for electrochemical measurement of glucose comprising:

providing a free-type flavin compound consisting of flavin mononucleotide, lumichrome, flavin adenine dinucleotide, or lumiflavin, bringing a sample comprising glucose, in contact with the free-type flavin compound, and a purified FAD-dependent glucose oxidase or a purified FAD-dependent glucose dehydrogenase to provide a measurement system; and carrying out an electric current measurement on said measurement system by bringing said measurement system into contact with an electrode, wherein with regard to the method:

(i) said measurement system does not contain an artificial electron mediator capable of accepting an electron on its own from the purified FAD-dependent glucose oxidase or the purified FAD-dependent glucose dehydrogenase; and (ii) said measurement system does not contain a water-insoluble electron mediator capable of accepting an electron on its own from the purified FAD-dependent glucose oxidase or the purified FAD-dependent glucose dehydrogenase; and further said measurement system does not contain an electron mediator capable of accepting an electron on its own from the purified FAD-dependent glucose oxidase or the purified FAD-dependent glucose dehydrogenase and having an oxidoreduction potential of 0.2 V or higher;

wherein the free-type flavin compound is present in the sample in free form and is separate from the purified FAD-dependent glucose oxidase or the purified FAD-dependent glucose dehydrogenase, wherein the purified FAD-dependent glucose oxidase is a holoenzyme or the purified FAD-dependent glucose dehydrogenase is a holoenzyme, and wherein, in the presence of glucose, the free-type flavin compound accepts an electron from the purified FAD-dependent glucose oxidase or the purified FAD-dependent glucose dehydrogenase thereby becoming reduced, and then transfers the electron to the electrode whereby the free-type flavin compound returns to an oxidized form.

7. The method of claim 6, further comprising the step of applying a voltage to the sample to determine the presence of glucose.

8. The method according to claim 6, wherein the free-type flavin compound has an oxidoreduction potential that is higher than an oxidoreduction potential of a FAD molecule within the purified FAD-dependent glucose oxidase or within the purified FAD-dependent glucose dehydrogenase.

* * * * *

SEQUENCE LISTING

```
<160> NUMBER OF SEQ ID NOS: 12

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365
```

-continued

```
Ala Gln Glu Gln Arg Glu Glu Tyr Glu Ala Asn Lys Thr Gly Ile Trp
    370                 375                 380

Ala Thr Ala Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Thr Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn
```

<210> SEQ ID NO 2
<211> LENGTH: 1926
<212> TYPE: DNA
<213> ORGANISM: Mucor prainii

<400> SEQUENCE: 2

```
atgaagatca cagctgccat tatcactgtt gccacagcat ttgcttcttt tgcttctgct      60

caacaagaca caaattcttc ctcaactgat acttatgatt atgttatcgt tggcggcggt     120

gtagctggtt tggctttggc tagtcgtatc tctgaaaaca aggatgtcac tgttgctgtt     180

ctcgagtccg gtcctaatgc caatgataga tttgttgttt atgctcctgg catgtatggc     240

caagctgttg gcactgatct ctgtcctctc attcctacta ctcctcaaga aaatatgggc     300

aacagaagtc tcacaatcgc tactggtaga ttgctcggtg gtggcagtgc tattaatggt     360

ctcgtttgga cccgtggtgg cttgaaggat tacgatgctt gggaggagct cggtaaccct     420

ggatggaacg gtgccaactt gttcaagtac tttaagaagg tcgaaaactt cactcctcct     480

actcctgccc aaattgaata cggcgctact tatcagaaaa gtgctcatgg caagaaggga     540
```

-continued

```
cctattgatg tctctttcac gaactacgag ttctctcaat ctgctagctg gaacgcctca    600

ctcgaaaccc ttgatttcac tgcacttcct gatatcttga acggtacttt ggccggttac    660

tctaccactc ccaacatttt ggaccctgag actgttcaac gtgttgattc ctatactggt    720

tacattgctc cttacactag ccgtaacaac ctcaatgttt tggccaacca taccgtctcc    780

cgcattcaat ttgctcccaa gaatggtagc gaacctctca aggctaccgg tgttgaatgg    840

tatcccactg gcaacaagaa tcaaaagcaa attatcaagg cccgttatga agttatcatc    900

tcatctggtg ccattggtag tcctaagctt ttggaaatct ctggtatcgg taataaggat    960

atcgtctctg ctgctggtgt cgagtccttg attgacttgc ctggcgttgg ttccaacatg   1020

caagatcacg ttcatgctat cactgtctct actaccaata ttactggcta tactaccaac   1080

agcgtctttg tcaatgaaac ccttgcccaa gaacaaagag aagaatatga agccaacaag   1140

actggtatct gggctactgc tcccaacaac ctcggttatc ctacgcccga acaactcttc   1200

aatggcaccg aattcgtttc tggaaaggag tttgctgaca agattcgtaa ctctactgat   1260

gaatgggcca actattatgc ttccaccaac gcctccaatg tcgagttatt aaagaagcaa   1320

tatgctattg tcgcctctcg ttacgaagag aactacttgt ctcctattga aatcaacttc   1380

actcctggtt atgagggtag cggtaatgtc gatttgcaaa acaacaagta ccaaactgtc   1440

aaccatgtct tgattgctcc tttaagtcgt ggttatactc acattaactc ttctgatgtg   1500

gaggatcatt ctgtcattaa tccccaatac tactctcatc ctatggatat tgatgtccat   1560

atcgcttcca ctaaacttgc tcgcgaaatc atcactgcct ctcccggtct tggtgacatt   1620

aacagtggcg aaaccgaacc cggtatgaat attacttctg aagacgacct tagatcttgg   1680

ttgagtaata atgtccgttc tgactggcat cctgttggta cttgtgctat gcttcccaag   1740

gaattaggtg gtgttgtcag ccccgctctc atggtttacg gcacttccaa cttgcgtgtt   1800

gttgatgctt cgattatgcc cctcgaagtc tcttctcatt tgatgcaacc cacctacggt   1860

attgctgaga aggctgctga cattattaag aatttctaca agactcaaca caagaaccaa   1920

aattag                                                              1926


<210> SEQ ID NO 3
<211> LENGTH: 641
<212> TYPE: PRT
<213> ORGANISM: Mucor prainii

<400> SEQUENCE: 3

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125
```

-continued

```
Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380

Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540
```

-continued

Ile Glu Pro Gly Met Asn Ile Thr Ser Asp Asp Asp Val Arg Lys Trp
545 550 555 560

Leu Ser Asn Asn Val Arg Ser Asp Trp His Pro Val Gly Thr Cys Ala
565 570 575

Met Leu Pro Lys Glu Leu Gly Gly Val Val Ser Pro Ala Leu Met Val
580 585 590

Tyr Gly Thr Ser Asn Leu Arg Val Val Asp Ala Ser Ile Met Pro Leu
595 600 605

Glu Val Ser Ser His Leu Met Gln Pro Thr Tyr Gly Ile Ala Glu Lys
610 615 620

Ala Ala Asp Ile Ile Lys Asn Phe Tyr Lys Thr Gln His Lys Asn Gln
625 630 635 640

Asn

<210> SEQ ID NO 4
<211> LENGTH: 1926
<212> TYPE: DNA
<213> ORGANISM: Mucor prainii

<400> SEQUENCE: 4
atgaagatca cagctgccat tatcactgtt gccacagcat ttgcttcttt tgcttctgct 60
caacaagaca caaattcttc ctcaactgat acttatgatt atgttatcgt tggcggcggt 120
gtagctggtt tggctttggc tagtcgtatc tctgaaaaca aggatgtcac tgttgctgtt 180
ctcgagtccg gtccttatgc cggtgataga tttgttgttt atgctcctgg catgtatggc 240
caagctgttg gcactgatct cgctcctctc attcctacta ctcctcaaga aaatatgggc 300
aacagaagtc tcacaatcgc tactggtaga ttgctcggtg gtggcagtgc tattaatggt 360
ctcgtttgga cccgtggtgg cttgaaggat tacgatgctt gggaggagct cggtaaccct 420
ggatggaacg gtgccaactt gttcaagtac tttaagaagg tcgaaaactt cactcctcct 480
actcctgccc aaattgaata cggcgctact tatcagaaaa gtgctcatgg caagaaggga 540
cctattgatg tctctttcac gaactacgag ttctctcaat ctgctagctg gaacgcctca 600
ctcgaaaccc ttgatttcac tgcacttcct gatatcttga acggtacttt ggccggttac 660
tctaccactc ccaacatttt ggaccctgag actgttcgac gtgttgattc ctatactggt 720
tacattgctc cttacactag ccgtaacaac ctcaatgttt tggccaacca taccgtctcc 780
cgcattcaat ttgctcccaa gaatggtagc gaacctctca aggctaccgg tgttgaatgg 840
tatcccactg gcaacaagaa tcaaaagcaa attatcaagg cccgttatga agttatcatc 900
tcatctggtg ccattggtag tcctaagctt ttggaaatct ctggtatcgg taataaggat 960
atcgtctctg ctgctggtgt cgagtccttg attgacttgc ctggcgttgg ttccaacatg 1020
caagatcacg ttcatgctat cactgtctct actaccaata ttactggcta tactaccaac 1080
agcgtctttg tcaatgaaac ccttgcccaa gaacaaagag aagaatatga agccaacaag 1140
actggtatct gggctacttg tcccaacaac ctcggttatc ctacgcccga acaactcttc 1200
aatggcaccg aattcgtttc tggaaaggag tttgctgaca agattcgtaa ctctactgat 1260
gaatgggcca actattatgc ttccaccaac gcctccaatg tcgagttatt aaagaagcaa 1320
tatgctattg tcgcctctcg ttacgaagag aactacttgt ctcctattga aatcaacttc 1380
actcctggtt atgagggtag cggtaatgtc gatttgcaaa acaacaagta ccaaactgtc 1440
aaccatgtct tgattgctcc tttaagtcgt ggttatactc acattaactc ttctgatgtg 1500
gaggatcatt ctgtcattaa tccccaatac tactctcatc ctatggatat tgatgtccat 1560

```
atcgcttcca ctaaacttgc tcgcgaaatc atcactgcct ctcccggtct tggtgacatt   1620

aacagtggcg aaatcgaacc cggtatgaat attacttctg acgacgacgt tagaaaatgg   1680

ttgagtaata atgtccgttc tgactggcat cctgttggta cttgtgctat gcttcccaag   1740

gaattaggtg gtgttgtcag ccccgctctc atggtttacg gcacttccaa cttgcgtgtt   1800

gttgatgctt cgattatgcc ccctcgaagtc tcttctcatt tgatgcaacc cacctacggt  1860

attgctgaga aggctgctga cattattaag aatttctaca agactcaaca caagaaccaa   1920

aattag                                                              1926
```

<210> SEQ ID NO 5
<211> LENGTH: 641
<212> TYPE: PRT
<213> ORGANISM: Mucor prainii

<400> SEQUENCE: 5

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Cys His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Cys Gly Thr Leu Ala Gly Tyr Ser Thr Thr Pro
    210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300
```

-continued

```
Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380

Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Asp Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Asp Asp Asp Val Arg Lys Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn
```

<210> SEQ ID NO 6
<211> LENGTH: 1926
<212> TYPE: DNA
<213> ORGANISM: Mucor prainii

<400> SEQUENCE: 6

```
atgaagatca cagctgccat tatcactgtt gccacagcat ttgcttcttt tgcttctgct     60

caacaagaca caaattcttc ctcaactgat acttatgatt atgttatcgt tggcggcggt    120

gtagctggtt tggctttggc tagtcgtatc tctgaaaaca aggatgtcac tgttgctgtt    180
```

-continued ctcgagtccg gtccttatgc cggtgataga tttgttgttt atgctcctgg catgtatggc 240
caagctgttg gcactgatct cgctcctctc attcctacta ctcctcaaga aaatatgggc 300
aacagaagtc tcacaatcgc tactggtaga ttgctcggtg gtggcagtgc tattaatggt 360
ctcgtttgga cccgtggtgg cttgaaggat tacgatgctt gggaggagct cggtaaccct 420
ggatggaacg gtgccaactt gttcaagtac tttaagaagg tcgaaaactt cactcctcct 480
actcctgccc aaattgaata cggcgctact tatcagaaaa gttgtcatgg caagaaggga 540
cctattgatg tctctttcac gaactacgag ttctctcaat ctgctagctg gaacgcctca 600
ctcgaaaccc ttgatttcac tgcacttcct gatatcttgt gcggtacttt ggccggttac 660
tctaccactc ccaacatttt ggaccctgag actgttcgac gtgttgattc ctatactggt 720
tacattgctc cttacactag ccgtaacaac ctcaatgttt tggccaacca taccgtctcc 780
cgcattcaat ttgctcccaa gaatggtagc gaacctctca aggctaccgg tgttgaatgg 840
tatcccactg gcaacaagaa tcaaaagcaa attatcaagg cccgttatga agttatcatc 900
tcatctggtg ccattggtag tcctaagctt ttggaaatct ctggtatcgg taataaggat 960
atcgtctctg ctgctggtgt cgagtccttg attgacttgc ctggcgttgg ttccaacatg 1020
caagatcacg ttcatgctat cactgtctct actaccaata ttactggcta tactaccaac 1080
agcgtctttg tcaatgaaac ccttgcccaa gaacaaagag aagaatatga agccaacaag 1140
actggtatct gggctacttg tcccaacaac ctcggttatc ctacgcccga acaactcttc 1200
aatggcaccg aattcgtttc tggaaaggag tttgctgaca agattcgtaa ctctactgat 1260
gaatgggcca actattatgc ttccaccaac gcctccaatg tcgagttatt aaagaagcaa 1320
tatgctattg tcgcctctcg ttacgaagag aactacttgt ctcctattga aatcaacttc 1380
actcctggtt atgaggacag cggtaatgtc gatttgcaaa acaacaagta ccaaactgtc 1440
aaccatgtct tgattgctcc tttaagtcgt ggttatactc acattaactc ttctgatgtg 1500
gaggatcatt ctgtcattaa tccccaatac tactctcatc ctatggatat tgatgtccat 1560
atcgcttcca ctaaacttgc tcgcgaaatc atcactgcct ctcccggtct tggtgacatt 1620
aacagtggcg aaatcgaacc cggtatgaat attacttctg acgacgacgt tagaaaatgg 1680
ttgagtaata atgtccgttc tgactggcat cctgttggta cttgtgctat gcttcccaag 1740
gaattaggtg gtgttgtcag ccccgctctc atggtttacg gcacttccaa cttgcgtgtt 1800
gttgatgctt cgattatgcc cctcgaagtc tcttctcatt tgatgcaacc cacctacggt 1860
attgctgaga aggctgctga cattattaag aatttctaca agactcaaca caagaaccaa 1920
aattag 1926

<210> SEQ ID NO 7
<211> LENGTH: 30
<212> TYPE: DNA
<213> ORGANISM: Artificial
<220> FEATURE:
<223> OTHER INFORMATION: synthetic

<400> SEQUENCE: 7
tatcagaaaa gttgtcatgg caagaaggga 30

<210> SEQ ID NO 8
<211> LENGTH: 30
<212> TYPE: DNA
<213> ORGANISM: Artificial
<220> FEATURE:

-continued

```
<223> OTHER INFORMATION: synthetic

<400> SEQUENCE: 8

agagacatca ataggtccct tcttgccatg                                        30


<210> SEQ ID NO 9
<211> LENGTH: 30
<212> TYPE: DNA
<213> ORGANISM: Artificial
<220> FEATURE:
<223> OTHER INFORMATION: synthetic

<400> SEQUENCE: 9

cctgatatct tgtgcggtac tttggccggt                                        30


<210> SEQ ID NO 10
<211> LENGTH: 30
<212> TYPE: DNA
<213> ORGANISM: Artificial
<220> FEATURE:
<223> OTHER INFORMATION: synthetic

<400> SEQUENCE: 10

gggagtggta gagtaaccgg ccaaagtacc                                        30


<210> SEQ ID NO 11
<211> LENGTH: 30
<212> TYPE: DNA
<213> ORGANISM: Artificial
<220> FEATURE:
<223> OTHER INFORMATION: synthetic

<400> SEQUENCE: 11

cctggttatg aggacagcgg taatgtcgat                                        30


<210> SEQ ID NO 12
<211> LENGTH: 30
<212> TYPE: DNA
<213> ORGANISM: Artificial
<220> FEATURE:
<223> OTHER INFORMATION: synthetic

<400> SEQUENCE: 12

cttgttgttt tgcaaatcga cattaccgct                                        30
```